US009622859B2

(12) United States Patent
Lafontaine et al.

(10) Patent No.: US 9,622,859 B2
(45) Date of Patent: Apr. 18, 2017

(54) FILTER SYSTEM AND METHOD

(71) Applicant: BOSTON SCIENTIFIC SCIMED, INC., Maple Grove, MN (US)

(72) Inventors: Daniel M. Lafontaine, Plymouth, MN (US); Mark L. Jenson, Greenfield, MN (US); William J. Drasler, Minnetonka, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/604,125

(22) Filed: Jan. 23, 2015

(65) Prior Publication Data
US 2015/0142102 A1    May 21, 2015

Related U.S. Application Data

(63) Continuation of application No. 11/049,019, filed on Feb. 1, 2005, now abandoned.

(51) Int. Cl.
*A61M 29/00*    (2006.01)
*A61F 2/24*    (2006.01)
(Continued)

(52) U.S. Cl.
CPC ............ *A61F 2/2418* (2013.01); *A61F 2/013* (2013.01); *A61F 2/2433* (2013.01); *A61F 2/958* (2013.01); *A61F 2002/011* (2013.01); *A61F 2002/018* (2013.01); *A61F 2220/005* (2013.01); *A61F 2220/0066* (2013.01);
(Continued)

(58) Field of Classification Search
CPC ...... A61F 2/2418; A61F 2/2433; A61F 2/013; A61F 2220/005; A61F 2220/0066; A61F 2230/0069; A61F 2230/008; A61F 2230/0006; A61F 2002/018; A61F 2002/011; A61F 2/958
See application file for complete search history.

(56) References Cited

U.S. PATENT DOCUMENTS 3,671,979 A    6/1972    Moulopoulos
4,291,420 A    9/1981    Reul
(Continued)

FOREIGN PATENT DOCUMENTS

EP    0380666 A1    8/1990
EP    0466518 A2    1/1992
(Continued)

OTHER PUBLICATIONS

US 6,673,110, 01/2004, Alfieri et al. (withdrawn)
(Continued)

*Primary Examiner* — Amy R Weisberg
(74) *Attorney, Agent, or Firm* — Seager, Tufte & Wickhem LLP

(57) ABSTRACT

A filter system, comprising an elongate filter body defining a lumen and having a proximal end and a distal end. A valve can be provided defining a lumen and having a reversibly sealable opening for unidirectional flow of a fluid through the lumen. The valve can be adjoined proximal the distal end of the elongate filter body, wherein the elongate filter body filters the unidirectional flow of the fluid passing through the lumen of the valve and the lumen of the elongate filter body.

19 Claims, 11 Drawing Sheets

(51) Int. Cl.
*A61F 2/01* (2006.01)
*A61F 2/958* (2013.01)

(52) U.S. Cl.
CPC . *A61F 2230/0006* (2013.01); *A61F 2230/008* (2013.01); *A61F 2230/0069* (2013.01)

(56) References Cited

U.S. PATENT DOCUMENTS

| | | |
|---|---|---|
| 4,787,901 A | 11/1988 | Baykut |
| 4,872,874 A | 10/1989 | Taheri |
| 4,935,030 A | 6/1990 | Alonso |
| 4,994,077 A | 2/1991 | Dobben |
| 5,002,567 A | 3/1991 | Bona et al. |
| 5,141,491 A | 8/1992 | Bowald |
| 5,163,953 A | 11/1992 | Vince |
| 5,219,355 A | 6/1993 | Parodi et al. |
| 5,254,127 A | 10/1993 | Wholey et al. |
| 5,300,086 A * | 4/1994 | Gory .................... A61F 2/01 |
| | | 128/899 |
| 5,327,774 A | 7/1994 | Nguyen et al. |
| 5,332,402 A | 7/1994 | Teitelbaum |
| 5,370,685 A | 12/1994 | Stevens |
| 5,411,552 A | 5/1995 | Andersen et al. |
| 5,469,868 A | 11/1995 | Reger |
| 5,480,423 A | 1/1996 | Ravenscroft et al. |
| 5,500,014 A | 3/1996 | Quijano et al. |
| 5,545,214 A | 8/1996 | Stevens |
| 5,554,185 A | 9/1996 | Block et al. |
| 5,643,208 A | 7/1997 | Parodi |
| 5,693,087 A | 12/1997 | Parodi |
| 5,713,953 A | 2/1998 | Vallana et al. |
| 5,716,370 A | 2/1998 | Williamson, IV et al. |
| 5,735,859 A | 4/1998 | Fischell et al. |
| 5,741,326 A | 4/1998 | Solovay |
| 5,741,333 A | 4/1998 | Frid |
| 5,800,506 A | 9/1998 | Perouse |
| 5,824,061 A | 10/1998 | Quijano et al. |
| 5,879,320 A | 3/1999 | Cazenave |
| 5,895,419 A | 4/1999 | Tweden et al. |
| 5,910,170 A | 6/1999 | Reimink et al. |
| 6,007,557 A * | 12/1999 | Ambrisco .................. A61F 2/01 |
| | | 606/159 |
| 6,010,531 A | 1/2000 | Donlon et al. |
| 6,042,607 A | 3/2000 | Williamson, IV et al. |
| 6,139,575 A | 10/2000 | Shu et al. |
| 6,287,334 B1 | 9/2001 | Moll et al. |
| 6,312,447 B1 | 11/2001 | Grimes |
| 6,355,030 B1 | 3/2002 | Aldrich et al. |
| 6,402,780 B2 | 6/2002 | Williamson, IV et al. |
| 6,419,696 B1 | 7/2002 | Ortiz et al. |
| 6,425,916 B1 | 7/2002 | Garrison et al. |
| 6,440,164 B1 * | 8/2002 | DiMatteo .............. A61F 2/2412 |
| | | 623/1.24 |
| 6,451,054 B1 | 9/2002 | Stevens |
| 6,454,799 B1 | 9/2002 | Schreck |
| 6,461,366 B1 | 10/2002 | Seguin |
| 6,503,272 B2 | 1/2003 | Duerig et al. |
| 6,508,833 B2 | 1/2003 | Pavcnik et al. |
| 6,564,805 B2 | 5/2003 | Garrison et al. |
| 6,569,196 B1 | 5/2003 | Vesely |
| 6,602,286 B1 | 8/2003 | Strecker |
| 6,629,534 B1 | 10/2003 | St. Goar et al. |
| 6,635,085 B1 | 10/2003 | Caffey et al. |
| 6,666,885 B2 | 12/2003 | Moe |
| 6,666,886 B1 | 12/2003 | Tranquillo et al. |
| 6,669,725 B2 | 12/2003 | Scott |
| 6,673,090 B2 * | 1/2004 | Root .................. A61B 18/1492 |
| | | 606/200 |
| 6,673,109 B2 | 1/2004 | Cox |
| 6,676,698 B2 | 1/2004 | McGuckin, Jr. et al. |
| 6,676,702 B2 | 1/2004 | Mathis |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,692,512 B2 | 2/2004 | Jang |
| 6,695,866 B1 | 2/2004 | Kuehn et al. |
| 6,695,878 B2 | 2/2004 | McGuckin, Jr. et al. |
| 6,709,456 B2 | 3/2004 | Langberg et al. |
| 6,709,457 B1 | 3/2004 | Otte et al. |
| 6,716,241 B2 | 4/2004 | Wilder et al. |
| 6,716,244 B2 | 4/2004 | Klaco |
| 6,719,767 B1 | 4/2004 | Kimblad |
| 6,719,784 B2 | 4/2004 | Henderson |
| 6,719,786 B2 | 4/2004 | Ryan et al. |
| 6,719,787 B2 | 4/2004 | Cox |
| 6,719,788 B2 | 4/2004 | Cox |
| 6,719,789 B2 | 4/2004 | Cox |
| 6,719,790 B2 | 4/2004 | Brendzel et al. |
| 6,723,038 B1 | 4/2004 | Schroeder et al. |
| 6,723,122 B2 | 4/2004 | Yang et al. |
| 6,723,123 B1 | 4/2004 | Kazatchkov et al. |
| 6,726,715 B2 | 4/2004 | Sutherland |
| 6,726,716 B2 | 4/2004 | Marquez |
| 6,726,717 B2 | 4/2004 | Alfieri et al. |
| 6,730,118 B2 | 5/2004 | Spenser et al. |
| 6,730,121 B2 | 5/2004 | Ortiz et al. |
| 6,730,122 B1 | 5/2004 | Pan et al. |
| 6,736,845 B2 | 5/2004 | Marquez et al. |
| 6,736,846 B2 | 5/2004 | Cox |
| 6,749,630 B2 | 6/2004 | McCarthy et al. |
| 6,752,813 B2 | 6/2004 | Goldfarb et al. |
| 6,752,828 B2 | 6/2004 | Thornton |
| 6,755,857 B2 | 6/2004 | Peterson et al. |
| 6,761,734 B2 | 7/2004 | Suhr |
| 6,761,735 B2 | 7/2004 | Eberhardt et al. |
| 6,764,494 B2 | 7/2004 | Menz et al. |
| 6,764,508 B1 | 7/2004 | Roehe et al. |
| 6,764,509 B2 | 7/2004 | Chinn et al. |
| 6,764,510 B2 | 7/2004 | Vidlund et al. |
| 6,767,362 B2 | 7/2004 | Schreck |
| 6,769,434 B2 | 8/2004 | Liddicoat et al. |
| 6,770,083 B2 | 8/2004 | Seguin |
| 6,780,200 B2 | 8/2004 | Jansen |
| 6,786,924 B2 | 9/2004 | Ryan et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,231 B2 | 9/2004 | Liddicoat et al. |
| 6,793,673 B2 | 9/2004 | Kowalsky et al. |
| 6,797,000 B2 | 9/2004 | Simpson et al. |
| 6,797,001 B2 | 9/2004 | Mathis et al. |
| 6,797,002 B2 | 9/2004 | Spence et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,810,882 B2 | 11/2004 | Langberg et al. |
| 6,821,297 B2 | 11/2004 | Snyders |
| 6,824,562 B2 | 11/2004 | Mathis et al. |
| 6,830,584 B1 | 12/2004 | Seguin |
| 6,830,585 B1 | 12/2004 | Artof et al. |
| 6,837,902 B2 | 1/2005 | Nguyen et al. |
| 6,840,246 B2 | 1/2005 | Downing |
| 6,840,957 B2 | 1/2005 | DiMatteo et al. |
| 6,846,324 B2 | 1/2005 | Stobie |
| 6,846,325 B2 | 1/2005 | Liddicoat |
| 6,858,039 B2 | 2/2005 | McCarthy |
| 6,869,444 B2 | 3/2005 | Gabbay |
| 6,872,226 B2 | 3/2005 | Cali et al. |
| 6,875,224 B2 | 4/2005 | Grimes |
| 6,875,230 B1 | 4/2005 | Morita et al. |
| 6,875,231 B2 | 4/2005 | Anduiza et al. |
| 6,881,199 B2 | 4/2005 | Wilk et al. |
| 6,881,224 B2 | 4/2005 | Kruse et al. |
| 6,883,522 B2 | 4/2005 | Spence et al. |
| 6,890,352 B1 | 5/2005 | Lentell |
| 6,890,353 B2 | 5/2005 | Cohn et al. |
| 6,893,459 B1 | 5/2005 | Macoviak |
| 6,893,460 B2 | 5/2005 | Spenser et al. |
| 6,896,700 B2 | 5/2005 | Lu et al. |
| 6,902,576 B2 | 6/2005 | Drasler et al. |
| 6,908,478 B2 | 6/2005 | Alferness et al. |
| 6,908,481 B2 | 6/2005 | Cribier |
| 6,911,043 B2 | 6/2005 | Myers et al. |

(56) References Cited

U.S. PATENT DOCUMENTS

| | | |
|---|---|---|
| 6,913,608 B2 | 7/2005 | Liddicoat et al. |
| 6,916,338 B2 | 7/2005 | Speziali |
| 6,918,917 B1 | 7/2005 | Nguyen et al. |
| 6,921,407 B2 | 7/2005 | Nguyen et al. |
| 6,921,811 B2 | 7/2005 | Zamora et al. |
| 6,926,715 B1 | 8/2005 | Hauck et al. |
| 6,926,730 B1 | 8/2005 | Nguyen et al. |
| 6,929,653 B2 | 8/2005 | Strecter |
| 6,932,838 B2 | 8/2005 | Schwartz et al. |
| 6,936,067 B2 | 8/2005 | Buchanan |
| 6,939,359 B2 | 9/2005 | Tu et al. |
| 6,942,694 B2 | 9/2005 | Liddicoat et al. |
| 6,945,957 B2 | 9/2005 | Freyman |
| 6,945,978 B1 | 9/2005 | Hyde |
| 6,945,996 B2 | 9/2005 | Sedransk |
| 6,945,997 B2 | 9/2005 | Huynh et al. |
| 6,949,122 B2 | 9/2005 | Adams et al. |
| 6,951,571 B1 | 10/2005 | Srivastava |
| 6,951,573 B1 | 10/2005 | Dilling |
| 6,953,332 B1 | 10/2005 | Kurk et al. |
| 6,955,689 B2 | 10/2005 | Ryan et al. |
| 6,958,076 B2 | 10/2005 | Acosta et al. |
| 6,962,605 B2 | 11/2005 | Cosgrove et al. |
| 6,964,682 B2 | 11/2005 | Nguyen-Thien-Nhon et al. |
| 6,964,683 B2 | 11/2005 | Kowalsky et al. |
| 6,964,684 B2 | 11/2005 | Ortiz et al. |
| 6,966,925 B2 | 11/2005 | Stobie |
| 6,966,926 B2 | 11/2005 | Mathis |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,995 B2 | 12/2005 | Mathis et al. |
| 6,979,350 B2 | 12/2005 | Moll et al. |
| 6,986,775 B2 | 1/2006 | Morales et al. |
| 6,989,027 B2 | 1/2006 | Allen et al. |
| 6,989,028 B2 | 1/2006 | Lashinski et al. |
| 6,997,950 B2 | 2/2006 | Chawla |
| 6,997,951 B2 | 2/2006 | Solem et al. |
| 7,004,176 B2 | 2/2006 | Lau |
| 7,007,396 B2 | 3/2006 | Rudko et al. |
| 7,011,669 B2 | 3/2006 | Kimblad |
| 7,011,681 B2 | 3/2006 | Vesely |
| 7,011,682 B2 | 3/2006 | Lashinski et al. |
| 7,018,406 B2 | 3/2006 | Seguin et al. |
| 7,018,407 B1 | 3/2006 | Wright et al. |
| 7,018,408 B2 | 3/2006 | Bailey et al. |
| 7,022,134 B1 | 4/2006 | Quijano et al. |
| 7,025,780 B2 | 4/2006 | Gabbay |
| 7,033,390 B2 | 4/2006 | Johnson et al. |
| 7,037,333 B2 | 5/2006 | Myers et al. |
| 7,037,334 B1 | 5/2006 | Hlavka et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,044,967 B1 | 5/2006 | Solem et al. |
| 7,048,754 B2 | 5/2006 | Martin et al. |
| 7,048,757 B2 | 5/2006 | Shaknovich |
| 7,052,487 B2 | 5/2006 | Cohn et al. |
| 7,052,507 B2 | 5/2006 | Wakuda et al. |
| 7,063,722 B2 | 6/2006 | Marquez |
| 7,066,954 B2 | 6/2006 | Ryan et al. |
| 7,070,616 B2 | 7/2006 | Majercak et al. |
| 7,070,618 B2 | 7/2006 | Streeter |
| 7,077,862 B2 | 7/2006 | Vidlund et al. |
| 7,081,131 B2 | 7/2006 | Thornton |
| 7,087,064 B1 | 8/2006 | Hyde |
| 7,089,051 B2 | 8/2006 | Javerud et al. |
| 7,090,695 B2 | 8/2006 | Solem et al. |
| 7,854,755 B2 * | 12/2010 | Lafontaine ....... A61B 17/32075 |
| | | 606/170 |
| 7,959,666 B2 * | 6/2011 | Salahieh ................ A61F 2/2418 |
| | | 623/1.26 |
| 7,988,724 B2 * | 8/2011 | Salahieh ............ A61B 17/0644 |
| | | 623/2.12 |
| 8,012,198 B2 * | 9/2011 | Hill ....................... A61F 2/2418 |
| | | 623/1.24 |
| 8,460,368 B2 * | 6/2013 | Taylor ................... A61F 2/2418 |
| | | 623/2.11 |
| 8,747,458 B2 * | 6/2014 | Tuval ........................ A61F 2/24 |
| | | 623/1.11 |
| 2002/0013571 A1 | 1/2002 | Goldfarb et al. |
| 2002/0026216 A1 | 2/2002 | Grimes |
| 2002/0082630 A1 | 6/2002 | Menz et al. |
| 2002/0123802 A1 | 9/2002 | Snyders |
| 2002/0151970 A1 | 10/2002 | Garrison et al. |
| 2002/0183835 A1 | 12/2002 | Taylor et al. |
| 2002/0183838 A1 | 12/2002 | Liddicoat et al. |
| 2002/0198594 A1 | 12/2002 | Schreck |
| 2003/0050694 A1 | 3/2003 | Yang et al. |
| 2003/0055492 A1 * | 3/2003 | Shaolian ............... A61F 2/2418 |
| | | 623/1.24 |
| 2003/0130729 A1 | 7/2003 | Paniagua et al. |
| 2003/0163194 A1 | 8/2003 | Quijano et al. |
| 2003/0167071 A1 | 9/2003 | Martin et al. |
| 2003/0171806 A1 | 9/2003 | Mathis et al. |
| 2003/0199075 A1 | 10/2003 | Gabbay |
| 2003/0229394 A1 | 12/2003 | Ogle et al. |
| 2003/0229395 A1 | 12/2003 | Cox |
| 2003/0233142 A1 | 12/2003 | Morales et al. |
| 2003/0236568 A1 | 12/2003 | Hojeibane et al. |
| 2003/0236569 A1 | 12/2003 | Mathis et al. |
| 2004/0002719 A1 | 1/2004 | Oz et al. |
| 2004/0003819 A1 | 1/2004 | St. Goar et al. |
| 2004/0010305 A1 | 1/2004 | Alferness et al. |
| 2004/0015230 A1 | 1/2004 | Moll et al. |
| 2004/0015232 A1 | 1/2004 | Shu et al. |
| 2004/0015233 A1 | 1/2004 | Jansen |
| 2004/0019374 A1 | 1/2004 | Hojeibane et al. |
| 2004/0019377 A1 | 1/2004 | Taylor et al. |
| 2004/0019378 A1 | 1/2004 | Hlavka et al. |
| 2004/0024447 A1 | 2/2004 | Haverich |
| 2004/0024451 A1 | 2/2004 | Johnson et al. |
| 2004/0024452 A1 | 2/2004 | Kruse et al. |
| 2004/0030321 A1 | 2/2004 | Fangrow, Jr. |
| 2004/0030381 A1 | 2/2004 | Shu |
| 2004/0030382 A1 | 2/2004 | St. Goar et al. |
| 2004/0030405 A1 | 2/2004 | Carpentier et al. |
| 2004/0034380 A1 | 2/2004 | Woolfson et al. |
| 2004/0034411 A1 | 2/2004 | Quijano et al. |
| 2004/0039436 A1 | 2/2004 | Spenser et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0044403 A1 | 3/2004 | Bischoff et al. |
| 2004/0049207 A1 | 3/2004 | Goldfarb et al. |
| 2004/0049211 A1 | 3/2004 | Tremulis et al. |
| 2004/0049266 A1 | 3/2004 | Anduiza et al. |
| 2004/0059351 A1 | 3/2004 | Eigler et al. |
| 2004/0059411 A1 | 3/2004 | Strecker |
| 2004/0059412 A1 | 3/2004 | Lytle, IV et al. |
| 2004/0060161 A1 | 4/2004 | Leal et al. |
| 2004/0073301 A1 | 4/2004 | Donlon et al. |
| 2004/0073302 A1 | 4/2004 | Rourke et al. |
| 2004/0078072 A1 | 4/2004 | Tu et al. |
| 2004/0078074 A1 | 4/2004 | Anderson et al. |
| 2004/0082910 A1 | 4/2004 | Constantz et al. |
| 2004/0082923 A1 | 4/2004 | Field |
| 2004/0082991 A1 | 4/2004 | Nguyen et al. |
| 2004/0087975 A1 | 5/2004 | Lucatero et al. |
| 2004/0088045 A1 | 5/2004 | Cox |
| 2004/0088046 A1 | 5/2004 | Speziali |
| 2004/0092858 A1 | 5/2004 | Wilson et al. |
| 2004/0093060 A1 | 5/2004 | Seguin et al. |
| 2004/0093070 A1 | 5/2004 | Hojeibane et al. |
| 2004/0093080 A1 | 5/2004 | Helmus et al. |
| 2004/0097979 A1 | 5/2004 | Svanidze et al. |
| 2004/0098098 A1 | 5/2004 | McGuckin, Jr. et al. |
| 2004/0098112 A1 | 5/2004 | DiMatteo et al. |
| 2004/0102839 A1 | 5/2004 | Cohn et al. |
| 2004/0102840 A1 | 5/2004 | Solem et al. |
| 2004/0102842 A1 | 5/2004 | Jansen |
| 2004/0106976 A1 | 6/2004 | Bailey et al. |

(56) References Cited

U.S. PATENT DOCUMENTS

| | | |
|---|---|---|
| 2004/0106990 A1 | 6/2004 | Spence et al. |
| 2004/0106991 A1 | 6/2004 | Hopkins et al. |
| 2004/0111096 A1 | 6/2004 | Tu et al. |
| 2004/0117009 A1 | 6/2004 | Cali et al. |
| 2004/0122448 A1 | 6/2004 | Levine |
| 2004/0122512 A1 | 6/2004 | Navia et al. |
| 2004/0122513 A1 | 6/2004 | Navia et al. |
| 2004/0122514 A1 | 6/2004 | Fogarty et al. |
| 2004/0122515 A1 | 6/2004 | Chu |
| 2004/0122516 A1 | 6/2004 | Fogarty et al. |
| 2004/0127979 A1 | 7/2004 | Wilson et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0133220 A1 | 7/2004 | Lashinski et al. |
| 2004/0133267 A1 | 7/2004 | Lane |
| 2004/0133273 A1 | 7/2004 | Cox |
| 2004/0138742 A1 | 7/2004 | Myers et al. |
| 2004/0138743 A1 | 7/2004 | Myers et al. |
| 2004/0138744 A1 | 7/2004 | Lashinski et al. |
| 2004/0138745 A1 | 7/2004 | Macoviak et al. |
| 2004/0148018 A1 | 7/2004 | Carpentier et al. |
| 2004/0148019 A1 | 7/2004 | Vidlund et al. |
| 2004/0148020 A1 | 7/2004 | Vidlund et al. |
| 2004/0153052 A1 | 8/2004 | Mathis |
| 2004/0153146 A1 | 8/2004 | Lashinski et al. |
| 2004/0153147 A1 | 8/2004 | Mathis |
| 2004/0158321 A1 | 8/2004 | Reuter et al. |
| 2004/0162610 A1 | 8/2004 | Liska et al. |
| 2004/0167539 A1 | 8/2004 | Kuehn et al. |
| 2004/0167620 A1 | 8/2004 | Ortiz et al. |
| 2004/0172046 A1 | 9/2004 | Hlavka et al. |
| 2004/0176839 A1 | 9/2004 | Huynh et al. |
| 2004/0176840 A1 | 9/2004 | Langberg et al. |
| 2004/0181238 A1 | 9/2004 | Zarbatany et al. |
| 2004/0186444 A1 | 9/2004 | Daly et al. |
| 2004/0186558 A1 | 9/2004 | Pavcnik et al. |
| 2004/0186561 A1 | 9/2004 | McGuckin, Jr. et al. |
| 2004/0186563 A1 | 9/2004 | Lobbi |
| 2004/0186565 A1 | 9/2004 | Schreck |
| 2004/0186566 A1 | 9/2004 | Hindrichs et al. |
| 2004/0193191 A1 | 9/2004 | Starksen et al. |
| 2004/0193253 A1 | 9/2004 | Thorpe et al. |
| 2004/0193260 A1 | 9/2004 | Alferness et al. |
| 2004/0199155 A1 | 10/2004 | Mollenauer |
| 2004/0199183 A1 | 10/2004 | Oz et al. |
| 2004/0199191 A1 | 10/2004 | Schwartz |
| 2004/0204758 A1 | 10/2004 | Eberhardt et al. |
| 2004/0206363 A1 | 10/2004 | McCarthy et al. |
| 2004/0210240 A1 | 10/2004 | Saint |
| 2004/0210301 A1 | 10/2004 | Obermiller |
| 2004/0210303 A1 | 10/2004 | Sedransk |
| 2004/0210304 A1 | 10/2004 | Seguin et al. |
| 2004/0210305 A1 | 10/2004 | Shu et al. |
| 2004/0210306 A1 | 10/2004 | Quijano et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0220654 A1 | 11/2004 | Mathis et al. |
| 2004/0220657 A1 | 11/2004 | Nieminen et al. |
| 2004/0225322 A1 | 11/2004 | Garrison et al. |
| 2004/0225344 A1 | 11/2004 | Hoffa et al. |
| 2004/0225348 A1 | 11/2004 | Case et al. |
| 2004/0225352 A1 | 11/2004 | Osborne et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0225356 A1 | 11/2004 | Frater |
| 2004/0230117 A1 | 11/2004 | Tosaya et al. |
| 2004/0230297 A1 | 11/2004 | Thornton |
| 2004/0236411 A1 | 11/2004 | Sarac et al. |
| 2004/0236418 A1 | 11/2004 | Stevens |
| 2004/0236419 A1 | 11/2004 | Milo |
| 2004/0243153 A1 | 12/2004 | Liddicoat et al. |
| 2004/0243219 A1 | 12/2004 | Fischer et al. |
| 2004/0243227 A1 | 12/2004 | Starksen et al. |
| 2004/0243228 A1 | 12/2004 | Kowalsky et al. |
| 2004/0243230 A1 | 12/2004 | Navia et al. |
| 2004/0249452 A1 | 12/2004 | Adams et al. |
| 2004/0254600 A1 | 12/2004 | Zarbatany et al. |
| 2004/0254601 A1* | 12/2004 | Eskuri ............... A61F 2/013 606/200 |
| 2004/0254636 A1 | 12/2004 | Flagle et al. |
| 2004/0260276 A1 | 12/2004 | Rudko et al. |
| 2004/0260317 A1 | 12/2004 | Bloom et al. |
| 2004/0260322 A1 | 12/2004 | Rudko et al. |
| 2004/0260389 A1 | 12/2004 | Case et al. |
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0004583 A1 | 1/2005 | Oz et al. |
| 2005/0004667 A1 | 1/2005 | Swinford et al. |
| 2005/0010285 A1* | 1/2005 | Lambrecht ............ A61F 2/2427 623/2.18 |
| 2005/0010287 A1 | 1/2005 | Macoviak et al. |
| 2005/0015112 A1* | 1/2005 | Cohn ................... A61F 2/2412 606/200 |
| 2005/0021056 A1 | 1/2005 | St. Goar et al. |
| 2005/0021136 A1 | 1/2005 | Xie et al. |
| 2005/0027261 A1 | 2/2005 | Weaver et al. |
| 2005/0027348 A1 | 2/2005 | Case et al. |
| 2005/0027351 A1 | 2/2005 | Reuter et al. |
| 2005/0027353 A1 | 2/2005 | Alferness et al. |
| 2005/0033398 A1 | 2/2005 | Seguin |
| 2005/0033419 A1 | 2/2005 | Alferness et al. |
| 2005/0033446 A1 | 2/2005 | Deem et al. |
| 2005/0038506 A1 | 2/2005 | Webler et al. |
| 2005/0038507 A1 | 2/2005 | Alferness et al. |
| 2005/0043790 A1 | 2/2005 | Seguin |
| 2005/0043792 A1 | 2/2005 | Solem et al. |
| 2005/0049679 A1 | 3/2005 | Taylor et al. |
| 2005/0049692 A1 | 3/2005 | Numamoto et al. |
| 2005/0049696 A1 | 3/2005 | Siess et al. |
| 2005/0049697 A1 | 3/2005 | Sievers |
| 2005/0054977 A1 | 3/2005 | Laird et al. |
| 2005/0055079 A1 | 3/2005 | Duran |
| 2005/0055087 A1 | 3/2005 | Starksen |
| 2005/0055088 A1 | 3/2005 | Liddicoat et al. |
| 2005/0055089 A1 | 3/2005 | Macoviak et al. |
| 2005/0060029 A1 | 3/2005 | Le et al. |
| 2005/0060030 A1 | 3/2005 | Lashinski et al. |
| 2005/0065460 A1 | 3/2005 | Laird |
| 2005/0065550 A1 | 3/2005 | Starksen et al. |
| 2005/0065594 A1 | 3/2005 | Dimatteo et al. |
| 2005/0065597 A1 | 3/2005 | Lansac |
| 2005/0070998 A1 | 3/2005 | Rourke et al. |
| 2005/0075584 A1 | 4/2005 | Cali |
| 2005/0075659 A1 | 4/2005 | Realyvasquez et al. |
| 2005/0075662 A1* | 4/2005 | Pedersen ............ A61B 17/22 606/194 |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075723 A1 | 4/2005 | Schroeder et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080483 A1 | 4/2005 | Solem et al. |
| 2005/0085900 A1 | 4/2005 | Case et al. |
| 2005/0085903 A1 | 4/2005 | Lau |
| 2005/0085904 A1 | 4/2005 | Lemmon |
| 2005/0090846 A1 | 4/2005 | Pedersen et al. |
| 2005/0096735 A1 | 5/2005 | Hojeibane et al. |
| 2005/0096738 A1 | 5/2005 | Cali et al. |
| 2005/0096739 A1 | 5/2005 | Cao |
| 2005/0096740 A1 | 5/2005 | Langberg et al. |

(56) References Cited

U.S. PATENT DOCUMENTS

| | | |
|---|---|---|
| 2005/0101975 A1 | 5/2005 | Nguyen et al. |
| 2005/0102026 A1 | 5/2005 | Turner et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107872 A1 | 5/2005 | Mensah et al. |
| 2005/0113910 A1 | 5/2005 | Paniagua et al. |
| 2005/0119673 A1 | 6/2005 | Gordon et al. |
| 2005/0119734 A1 | 6/2005 | Spence et al. |
| 2005/0119735 A1 | 6/2005 | Spence et al. |
| 2005/0125011 A1 | 6/2005 | Spence et al. |
| 2005/0131438 A1 | 6/2005 | Cohn |
| 2005/0137449 A1 | 6/2005 | Nieminen et al. |
| 2005/0137450 A1 | 6/2005 | Aronson et al. |
| 2005/0137451 A1 | 6/2005 | Gordon et al. |
| 2005/0137676 A1* | 6/2005 | Richardson ............ A61F 2/2418 623/1.11 |
| 2005/0137681 A1 | 6/2005 | Shoemaker et al. |
| 2005/0137682 A1 | 6/2005 | Justino |
| 2005/0137685 A1 | 6/2005 | Nieminen et al. |
| 2005/0137686 A1* | 6/2005 | Salahieh ............... A61F 2/2418 623/2.11 |
| 2005/0137688 A1* | 6/2005 | Salahieh ............... A61F 2/2418 623/2.11 |
| 2005/0137689 A1* | 6/2005 | Salahieh ............... A61F 2/2418 623/2.11 |
| 2005/0137690 A1* | 6/2005 | Salahieh ............... A61F 2/2418 623/2.11 |
| 2005/0137691 A1* | 6/2005 | Salahieh ............... A61F 2/2418 623/2.11 |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137696 A1* | 6/2005 | Salahieh ................ A61F 2/013 623/2.11 |
| 2005/0137697 A1* | 6/2005 | Salahieh ............... A61F 2/2418 623/2.11 |
| 2005/0137698 A1* | 6/2005 | Salahieh ............... A61F 2/2418 623/2.11 |
| 2005/0137699 A1 | 6/2005 | Salahieh et al. |
| 2005/0137700 A1 | 6/2005 | Spence et al. |
| 2005/0137701 A1* | 6/2005 | Salahieh ............... A61F 2/2418 623/2.38 |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0143810 A1 | 6/2005 | Dauner et al. |
| 2005/0143811 A1 | 6/2005 | Realyvasquez |
| 2005/0149014 A1 | 7/2005 | Hauck et al. |
| 2005/0149179 A1 | 7/2005 | Mathis et al. |
| 2005/0149180 A1 | 7/2005 | Mathis et al. |
| 2005/0149181 A1 | 7/2005 | Eberhardt |
| 2005/0159810 A1 | 7/2005 | Filsoufi |
| 2005/0159811 A1 | 7/2005 | Lane |
| 2005/0165477 A1 | 7/2005 | Anduiza et al. |
| 2005/0165478 A1 | 7/2005 | Song |
| 2005/0171472 A1 | 8/2005 | Lutter |
| 2005/0171601 A1 | 8/2005 | Cosgrove et al. |
| 2005/0177227 A1 | 8/2005 | Heim et al. |
| 2005/0177228 A1 | 8/2005 | Solem et al. |
| 2005/0182483 A1 | 8/2005 | Osborne et al. |
| 2005/0184122 A1 | 8/2005 | Hlavka et al. |
| 2005/0187614 A1 | 8/2005 | Agnew |
| 2005/0187616 A1* | 8/2005 | Realyvasquez ....... A61F 2/2427 623/2.11 |
| 2005/0187617 A1 | 8/2005 | Navia |
| 2005/0192606 A1 | 9/2005 | Paul, Jr. et al. |
| 2005/0192665 A1 | 9/2005 | Spenser et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216039 A1 | 9/2005 | Lederman |
| 2005/0216077 A1 | 9/2005 | Mathis et al. |
| 2005/0216078 A1 | 9/2005 | Starksen et al. |
| 2005/0222675 A1 | 10/2005 | Sauter |
| 2005/0222678 A1 | 10/2005 | Lashinski et al. |
| 2005/0228422 A1 | 10/2005 | Machold et al. |
| 2005/0228479 A1 | 10/2005 | Pavcnik et al. |
| 2005/0228486 A1 | 10/2005 | Case et al. |
| 2005/0228494 A1 | 10/2005 | Marquez |
| 2005/0228495 A1 | 10/2005 | Macoviak |
| 2005/0228496 A1 | 10/2005 | Mensah et al. |
| 2005/0234541 A1 | 10/2005 | Hunt et al. |
| 2005/0234546 A1 | 10/2005 | Nugent et al. |
| 2005/0240200 A1 | 10/2005 | Bergheim |
| 2005/0240202 A1 | 10/2005 | Shennib et al. |
| 2005/0240255 A1 | 10/2005 | Schaeffer |
| 2005/0240259 A1 | 10/2005 | Sisken et al. |
| 2005/0240262 A1 | 10/2005 | White |
| 2005/0244460 A1 | 11/2005 | Alferiev et al. |
| 2005/0246013 A1 | 11/2005 | Gabbay |
| 2005/0251251 A1 | 11/2005 | Cribier |
| 2005/0256566 A1 | 11/2005 | Gabbay |
| 2005/0261704 A1 | 11/2005 | Mathis |
| 2005/0261759 A1 | 11/2005 | Lambrecht et al. |
| 2005/0267493 A1 | 12/2005 | Schreck et al. |
| 2005/0267560 A1 | 12/2005 | Bates |
| 2005/0267565 A1 | 12/2005 | Dave et al. |
| 2005/0267571 A1 | 12/2005 | Spence et al. |
| 2005/0267573 A9 | 12/2005 | Macoviak et al. |
| 2005/0267574 A1 | 12/2005 | Cohn et al. |
| 2005/0272969 A1 | 12/2005 | Alferness et al. |
| 2005/0273160 A1 | 12/2005 | Lashinski et al. |
| 2005/0278015 A1 | 12/2005 | Dave et al. |
| 2005/0283178 A1 | 12/2005 | Flagle et al. |
| 2005/0288779 A1 | 12/2005 | Shaoulian et al. |
| 2006/0000715 A1 | 1/2006 | Whitcher et al. |
| 2006/0004439 A1 | 1/2006 | Spenser et al. |
| 2006/0004442 A1 | 1/2006 | Spenser et al. |
| 2006/0009804 A1 | 1/2006 | Pederson |
| 2006/0009841 A1 | 1/2006 | McGuckin, Jr. et al. |
| 2006/0009842 A1 | 1/2006 | Huynh et al. |
| 2006/0013805 A1 | 1/2006 | Hebbel et al. |
| 2006/0013855 A1 | 1/2006 | Carpenter et al. |
| 2006/0015136 A1 | 1/2006 | Besselink |
| 2006/0015178 A1 | 1/2006 | Moaddeb et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020332 A1 | 1/2006 | Lashinski et al. |
| 2006/0020334 A1 | 1/2006 | Lashinski et al. |
| 2006/0020335 A1 | 1/2006 | Kowalsky et al. |
| 2006/0020336 A1 | 1/2006 | Liddicoat |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0025854 A1 | 2/2006 | Lashinski et al. |
| 2006/0025855 A1 | 2/2006 | Lashinski et al. |
| 2006/0025856 A1 | 2/2006 | Ryan et al. |
| 2006/0025857 A1 | 2/2006 | Bergheim et al. |
| 2006/0030747 A1 | 2/2006 | Kantrowitz et al. |
| 2006/0030866 A1 | 2/2006 | Schreck |
| 2006/0030882 A1 | 2/2006 | Adams et al. |
| 2006/0030885 A1 | 2/2006 | Hyde |
| 2006/0036317 A1 | 2/2006 | Vidlund et al. |
| 2006/0041305 A1 | 2/2006 | Lauterjung |
| 2006/0041306 A1 | 2/2006 | Vidlund et al. |
| 2006/0047297 A1 | 3/2006 | Case |
| 2006/0047338 A1 | 3/2006 | Jenson |
| 2006/0047343 A1 | 3/2006 | Oviatt et al. |
| 2006/0052804 A1 | 3/2006 | Mialhe |
| 2006/0052867 A1 | 3/2006 | Revuelta et al. |
| 2006/0058817 A1 | 3/2006 | Starksen et al. |
| 2006/0058865 A1 | 3/2006 | Case et al. |
| 2006/0058871 A1 | 3/2006 | Zakay et al. |
| 2006/0058889 A1 | 3/2006 | Case et al. |

(56) References Cited

U.S. PATENT DOCUMENTS

| | | |
|---|---|---|
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0064174 A1 | 3/2006 | Zadno |
| 2006/0069400 A1 | 3/2006 | Burnett et al. |
| 2006/0069429 A1 | 3/2006 | Spence et al. |
| 2006/0069430 A9 | 3/2006 | Rahdert et al. |
| 2006/0074483 A1 | 4/2006 | Schrayer |
| 2006/0074484 A1 | 4/2006 | Huber |
| 2006/0074485 A1 | 4/2006 | Realyvasquez |
| 2006/0085060 A1 | 4/2006 | Campbell |
| 2006/0089708 A1 | 4/2006 | Osse et al. |
| 2006/0095115 A1 | 5/2006 | Bladillah et al. |
| 2006/0095125 A1 | 5/2006 | Chinn et al. |
| 2006/0099326 A1 | 5/2006 | Keogh et al. |
| 2006/0100697 A1 | 5/2006 | Casanova |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0111660 A1 | 5/2006 | Wolf et al. |
| 2006/0111773 A1 | 5/2006 | Rittgers et al. |
| 2006/0111774 A1 | 5/2006 | Samkov et al. |
| 2006/0116572 A1 | 6/2006 | Case |
| 2006/0116756 A1 | 6/2006 | Solem et al. |
| 2006/0122686 A1 | 6/2006 | Gilad et al. |
| 2006/0122692 A1 | 6/2006 | Gilad et al. |
| 2006/0122693 A1 | 6/2006 | Biadillah et al. |
| 2006/0127443 A1 | 6/2006 | Helmus |
| 2006/0129235 A1 | 6/2006 | Seguin et al. |
| 2006/0129236 A1 | 6/2006 | McCarthy |
| 2006/0135476 A1 | 6/2006 | Kutryk et al. |
| 2006/0135964 A1 | 6/2006 | Vesely |
| 2006/0135967 A1 | 6/2006 | Realyvasquez |
| 2006/0136044 A1 | 6/2006 | Osborne |
| 2006/0136045 A1 | 6/2006 | Flagle et al. |
| 2006/0136052 A1 | 6/2006 | Vesely |
| 2006/0136054 A1 | 6/2006 | Berg et al. |
| 2006/0142846 A1 | 6/2006 | Pavcnik et al. |
| 2006/0142847 A1 | 6/2006 | Shaknovich |
| 2006/0142848 A1 | 6/2006 | Gabbay |
| 2006/0142854 A1 | 6/2006 | Alferness et al. |
| 2006/0149358 A1 | 7/2006 | Zilla et al. |
| 2006/0149360 A1 | 7/2006 | Schwammenthal et al. |
| 2006/0149367 A1 | 7/2006 | Sieracki |
| 2006/0149368 A1 | 7/2006 | Spence |
| 2006/0161133 A1 | 7/2006 | Laird et al. |
| 2006/0161248 A1 | 7/2006 | Case et al. |
| 2006/0161249 A1 | 7/2006 | Realyvasquez et al. |
| 2006/0161250 A1 | 7/2006 | Shaw |
| 2006/0167468 A1 | 7/2006 | Gabbay |
| 2006/0167541 A1 | 7/2006 | Lattouf |
| 2006/0167542 A1 | 7/2006 | Quintessenza |
| 2006/0167543 A1 | 7/2006 | Bailey et al. |
| 2006/0173490 A1* | 8/2006 | Lafontaine .............. A61F 2/013 606/200 |
| 2008/0269877 A1* | 10/2008 | Jenson .................... A61F 2/013 623/2.11 |
| 2010/0131056 A1* | 5/2010 | Lapeyre ................ A61F 2/2403 623/2.27 |

FOREIGN PATENT DOCUMENTS

| | | |
|---|---|---|
| FR | 2728457 A1 | 6/1996 |
| WO | 8800459 A1 | 1/1988 |
| WO | 9015582 A1 | 12/1990 |
| WO | 9501669 A1 | 1/1995 |
| WO | 9619159 A1 | 6/1996 |
| WO | 9803656 A1 | 1/1998 |
| WO | 9846115 A2 | 10/1998 |
| WO | 9904724 A1 | 2/1999 |
| WO | 0067679 A1 | 11/2000 |
| WO | 0115650 A1 | 3/2001 |
| WO | 0117462 A1 | 3/2001 |
| WO | 03047468 A1 | 6/2003 |
| WO | 03008443 A1 | 10/2003 |
| WO | 2004019825 A1 | 3/2004 |
| WO | 2004021893 A1 | 3/2004 |
| WO | 2004023980 A2 | 3/2004 |
| WO | 2004030568 A2 | 4/2004 |
| WO | 2004030569 A2 | 4/2004 |
| WO | 2004030570 A2 | 4/2004 |
| WO | 2004032724 A2 | 4/2004 |
| WO | 2004032796 A2 | 4/2004 |
| WO | 2004037128 A1 | 5/2004 |
| WO | 2004037317 A1 | 5/2004 |
| WO | 2004039432 A2 | 5/2004 |
| WO | 2004043265 A2 | 5/2004 |
| WO | 2004043273 A2 | 5/2004 |
| WO | 2004043293 A2 | 5/2004 |
| WO | 2004045370 A2 | 6/2004 |
| WO | 2004045378 A2 | 6/2004 |
| WO | 2004045463 A2 | 6/2004 |
| WO | 2004047677 A2 | 6/2004 |
| WO | 2004060217 A1 | 7/2004 |
| WO | 2004060470 A1 | 7/2004 |
| WO | 2004062725 A1 | 7/2004 |
| WO | 2004066803 A2 | 8/2004 |
| WO | 2004066826 A2 | 8/2004 |
| WO | 2004069287 A2 | 8/2004 |
| WO | 2004075789 A2 | 9/2004 |
| WO | 2004080352 A1 | 9/2004 |
| WO | 2004082523 A2 | 9/2004 |
| WO | 2004082527 A2 | 9/2004 |
| WO | 2004082528 A2 | 9/2004 |
| WO | 2004082536 A1 | 9/2004 |
| WO | 2004082537 A1 | 9/2004 |
| WO | 2004082538 A2 | 9/2004 |
| WO | 2004082757 A1 | 9/2004 |
| WO | 2004084746 A2 | 10/2004 |
| WO | 2004084770 A1 | 10/2004 |
| WO | 2004089246 A2 | 10/2004 |
| WO | 2004089250 A1 | 10/2004 |
| WO | 2004089253 A1 | 10/2004 |
| WO | 2004091449 A1 | 10/2004 |
| WO | 2004091454 A1 | 10/2004 |
| WO | 2004093638 A2 | 11/2004 |
| WO | 2004093726 A2 | 11/2004 |
| WO | 2004093728 A2 | 11/2004 |
| WO | 2004093730 A2 | 11/2004 |
| WO | 2004093745 A1 | 11/2004 |
| WO | 2004093935 A2 | 11/2004 |
| WO | 2004096100 A1 | 11/2004 |
| WO | 2004103222 A1 | 12/2004 |
| WO | 2004103223 A1 | 12/2004 |
| WO | 2004105584 A2 | 12/2004 |
| WO | 2004105651 A1 | 12/2004 |
| WO | 2004112582 A2 | 12/2004 |
| WO | 2004112585 A2 | 12/2004 |
| WO | 2004112643 A2 | 12/2004 |
| WO | 2004112652 A2 | 12/2004 |
| WO | 2004112657 A1 | 12/2004 |
| WO | 2004112658 A1 | 12/2004 |
| WO | 2005000152 A2 | 1/2005 |
| WO | 2005002424 A2 | 1/2005 |
| WO | 2005002466 A2 | 1/2005 |
| WO | 2005004753 A1 | 1/2005 |
| WO | 2005007017 A2 | 1/2005 |
| WO | 2005007018 A2 | 1/2005 |
| WO | 2005007036 A1 | 1/2005 |
| WO | 2005007037 A1 | 1/2005 |
| WO | 2005009285 A2 | 2/2005 |
| WO | 2005009286 A2 | 2/2005 |
| WO | 2005009505 A2 | 2/2005 |
| WO | 2005009506 A2 | 2/2005 |
| WO | 2005011473 A2 | 2/2005 |
| WO | 2005011534 A2 | 2/2005 |
| WO | 2005011535 A2 | 2/2005 |
| WO | 2005013860 A2 | 2/2005 |
| WO | 2005018507 A2 | 3/2005 |
| WO | 2005021063 A2 | 3/2005 |
| WO | 2005023155 A1 | 3/2005 |
| WO | 2005025644 A2 | 3/2005 |
| WO | 2005027790 A1 | 3/2005 |

(56) References Cited

FOREIGN PATENT DOCUMENTS

| | | |
|---|---|---|
| WO | 2005027797 A1 | 3/2005 |
| WO | 2005034812 A1 | 4/2005 |
| WO | 2005039428 A2 | 5/2005 |
| WO | 2005039452 A1 | 5/2005 |
| WO | 2005046488 A2 | 5/2005 |
| WO | 2005046528 A1 | 5/2005 |
| WO | 2005046529 A1 | 5/2005 |
| WO | 2005046530 A1 | 5/2005 |
| WO | 2005046531 A2 | 5/2005 |
| WO | 2005048883 A1 | 6/2005 |
| WO | 2005049103 A2 | 6/2005 |
| WO | 2005051226 A2 | 6/2005 |
| WO | 2005055811 A2 | 6/2005 |
| WO | 2005055883 A1 | 6/2005 |
| WO | 2005058206 A1 | 6/2005 |
| WO | 2005065585 A1 | 7/2005 |
| WO | 2005065593 A1 | 7/2005 |
| WO | 2005065594 A1 | 7/2005 |
| WO | 2005070342 A1 | 8/2005 |
| WO | 2005070343 A1 | 8/2005 |
| WO | 2005072654 A1 | 8/2005 |
| WO | 2005072655 A1 | 8/2005 |
| WO | 2005079706 A1 | 9/2005 |
| WO | 2005082288 A1 | 9/2005 |
| WO | 2005082289 A1 | 9/2005 |
| WO | 2005084595 A1 | 9/2005 |
| WO | 2005087139 A1 | 9/2005 |
| WO | 2005087140 A1 | 9/2005 |
| WO | 2006000763 A2 | 1/2006 |
| WO | 2006000776 A2 | 1/2006 |
| WO | 2006002492 A1 | 1/2006 |
| WO | 2006004679 A1 | 1/2006 |
| WO | 2006005015 A2 | 1/2006 |
| WO | 2006009690 A1 | 1/2006 |
| WO | 2006011127 A2 | 2/2006 |
| WO | 2006012011 A2 | 2/2006 |
| WO | 2006012013 A2 | 2/2006 |
| WO | 2006012038 A2 | 2/2006 |
| WO | 2006012068 A2 | 2/2006 |
| WO | 2006012322 A1 | 2/2006 |
| WO | 2006019498 A2 | 2/2006 |
| WO | 2006026371 A1 | 3/2006 |
| WO | 2006026377 A1 | 3/2006 |
| WO | 2006026912 A1 | 3/2006 |
| WO | 2006027499 A2 | 3/2006 |
| WO | 2006028821 A1 | 3/2006 |
| WO | 2006029062 A1 | 3/2006 |
| WO | 2006031436 A1 | 3/2006 |
| WO | 2006031469 A1 | 3/2006 |
| WO | 2006032051 A2 | 3/2006 |
| WO | 2006034245 A2 | 3/2006 |
| WO | 2006035415 A2 | 4/2006 |
| WO | 2006041505 A1 | 4/2006 |
| WO | 2006044679 A1 | 4/2006 |
| WO | 2006048664 A2 | 5/2006 |
| WO | 2006050459 A2 | 5/2006 |
| WO | 2006050460 A1 | 5/2006 |
| WO | 2006054107 A2 | 5/2006 |
| WO | 2006054930 A1 | 5/2006 |
| WO | 2006055982 A2 | 5/2006 |
| WO | 2006060546 A2 | 6/2006 |
| WO | 2006063108 A1 | 6/2006 |
| WO | 2006063181 A1 | 6/2006 |
| WO | 2006063199 A2 | 6/2006 |
| WO | 2006064490 A1 | 6/2006 |
| WO | 2006065212 A1 | 6/2006 |
| WO | 2006065930 A2 | 6/2006 |
| WO | 2006066148 A2 | 6/2006 |
| WO | 2006066150 A2 | 6/2006 |
| WO | 2006069094 A1 | 6/2006 |
| WO | 2006070372 A2 | 7/2006 |
| WO | 2006073628 A1 | 7/2006 |
| WO | 2006076890 A1 | 7/2006 |
| WO | 20060149360 | 7/2006 |

OTHER PUBLICATIONS

US 6,723,117, 04/2004, Menz et al. (withdrawn)
All non-patent literature documents and foreign patent documents have been previously uploaded in parent U.S. Appl. No. 11/049,019, filed Feb. 18, 2005.
European Office Action in related European Patent Application No. 06 717 435.9. Jul. 26, 2010. 6 pages.
All non-patent literature documents and foreign patent documents have been previously uploaded in U.S. Appl. No. parent 11/049,019, filed Feb. 18, 2005.

* cited by examiner

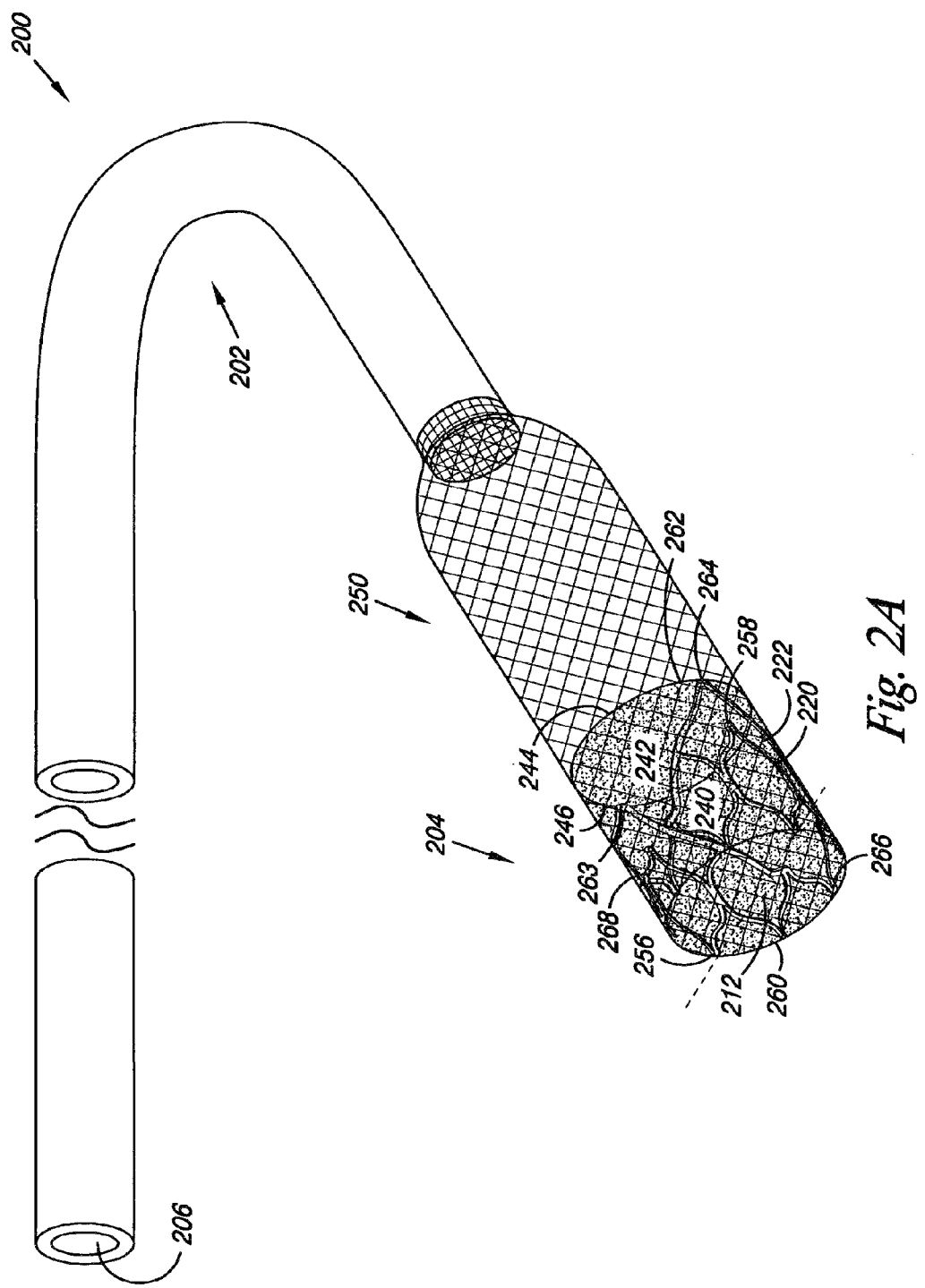

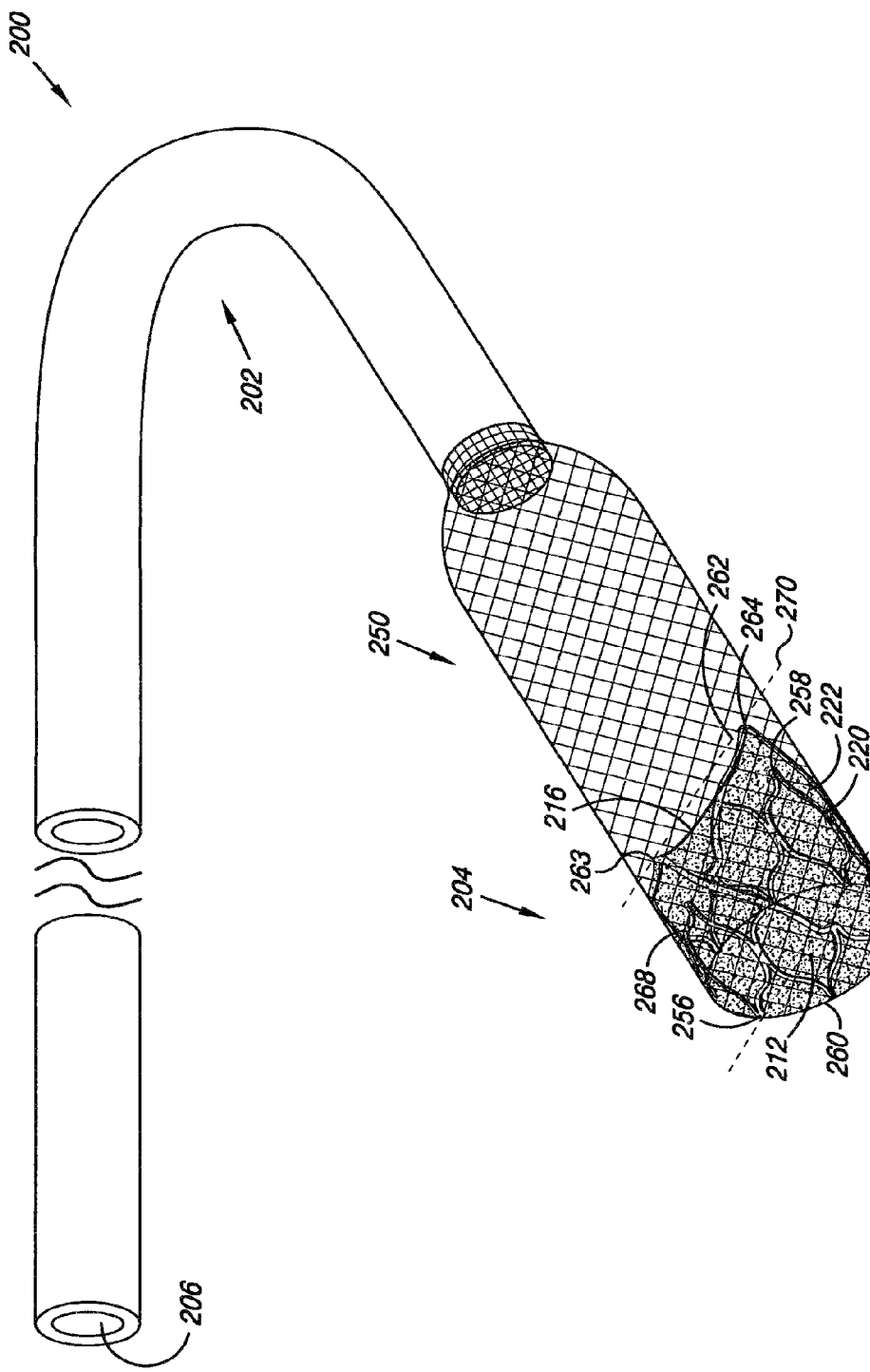

FILTER SYSTEM AND METHOD

RELATED APPLICATIONS

This application is a continuation of U.S. application Ser. No. 11/049,019, filed Feb. 1, 2005.

FIELD OF THE INVENTION

The present invention relates generally to apparatus, systems, and methods for use in a lumen; and more particularly to a valve and filter apparatus, system, and method for use in the vasculature system.

BACKGROUND OF THE INVENTION

Cardiac valves can become damaged and/or diseased for a variety of reasons. Damaged and/or diseased cardiac valves are grouped according to which valve or valves are involved, and the amount of blood flow that is disrupted by the damaged and/or diseased valve. The most common cardiac valve diseases occur in the mitral and aortic valves. Diseases of the tricuspid and pulmonary valves are fairly rare.

The aortic valve regulates the blood flow from the heart's left ventricle into the aorta. The aorta is the main artery that supplies oxygenated blood to the body. As a result, diseases of the aortic valve can have a significant impact on an individual's health. Examples of such diseases include aortic regurgitation and aortic stenosis.

Aortic regurgitation is also called aortic insufficiency or aortic incompetence. It is a condition in which blood flows backward from a widened or weakened aortic valve into the left ventricle of the heart. In its most serious form, aortic regurgitation is caused by an infection that leaves holes in the valve leaflets. Symptoms of aortic regurgitation may not appear for years. When symptoms do appear, it is because the left ventricle must work harder relative to an uncompromised aortic valve to make up for the backflow of blood. The ventricle eventually gets larger and fluid backs up.

Aortic stenosis is a narrowing or blockage of the aortic valve. Aortic stenosis occurs when the valve leaflets of the aorta become coated with deposits. The deposits change the shape of the leaflets and reduce blood flow through the valve. Again, the left ventricle has to work harder relative to an uncompromised aortic valve to make up for the reduced blood flow. Over time, the extra work can weaken the heart muscle.

BRIEF DESCRIPTION OF THE DRAWINGS

FIGS. 2A-2B illustrate another embodiment of a filter system.

DETAILED DESCRIPTION

Figure 1A:
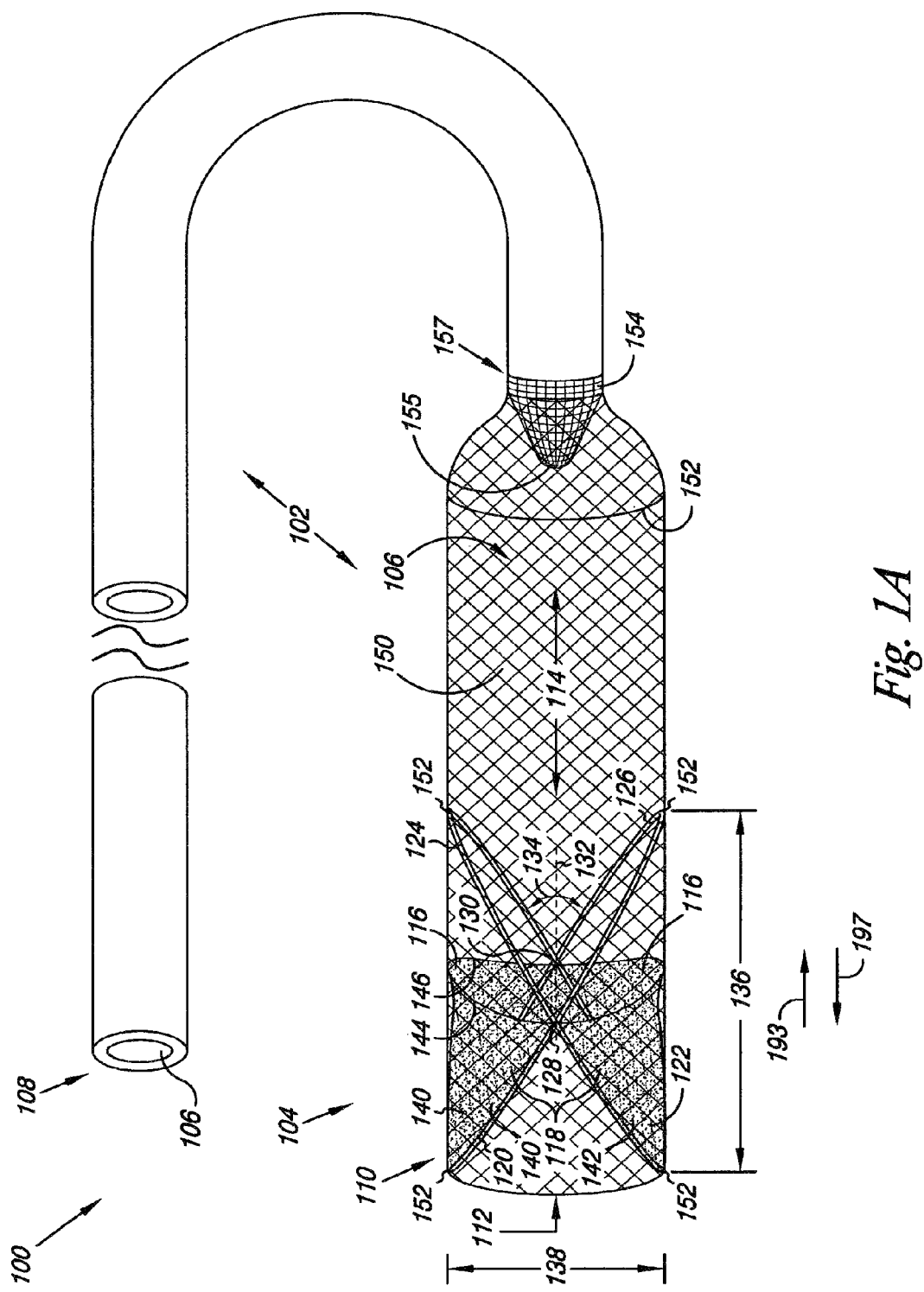
FIGS. 1A-1B illustrate an embodiment of a filter system.

Embodiments of the present invention are directed to a filter system and method for temporary placement and use in a lumen. Embodiments of the present invention are also directed to augmenting cardiac valve function while filtering fluid moving within the lumen. For example, the filter system and method can be used to temporarily replace, or augment, an incompetent valve in a body lumen and/or can be used as a temporary valve during a procedure to repair or to replace an incompetent valve with a prosthetic valve.

Embodiments of the filter system can further include a sheath that can be used to help position the filter system within a body lumen, such as an artery or a vein, through minimally-invasive techniques. In further embodiments, additional structures can be used in conjunction with the filter system. For example, catheters having tissue shearing capability, stent delivery capability, and prosthetic valve delivery capability can also be used in conjunction with the filter system to aid in the replacement of a diseased native valve with a prosthetic valve. In an additional embodiment, the sheath can include a deployment rod to extend and retract the cardiac valve and filter. After replacement or repair of a native valve, the filter system can be refracted into the lumen of the sheath.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of the filter system. In addition, the elements shown in the various embodiments are not necessarily to scale.

Various embodiments of the invention are illustrated in the figures. Generally, the filter system can be used to provide a temporary valve for replacement or repair of a diseased and/or damaged valve. Other embodiments can be used to provide a temporary valve and filter during a procedure to repair a diseased or damaged valve or replace a diseased and/or damaged valve with a permanent valve. For example, the placement of the valve and filter apparatus within a body lumen (e.g., within the aorta, adjacent the aortic valve), can help to provide for a temporary valve and filter to regulate fluid flow and filter particulate matter from fluid flowing through the aorta during transluminal cardiac valve repair and/or replacement.

Figure 1B:
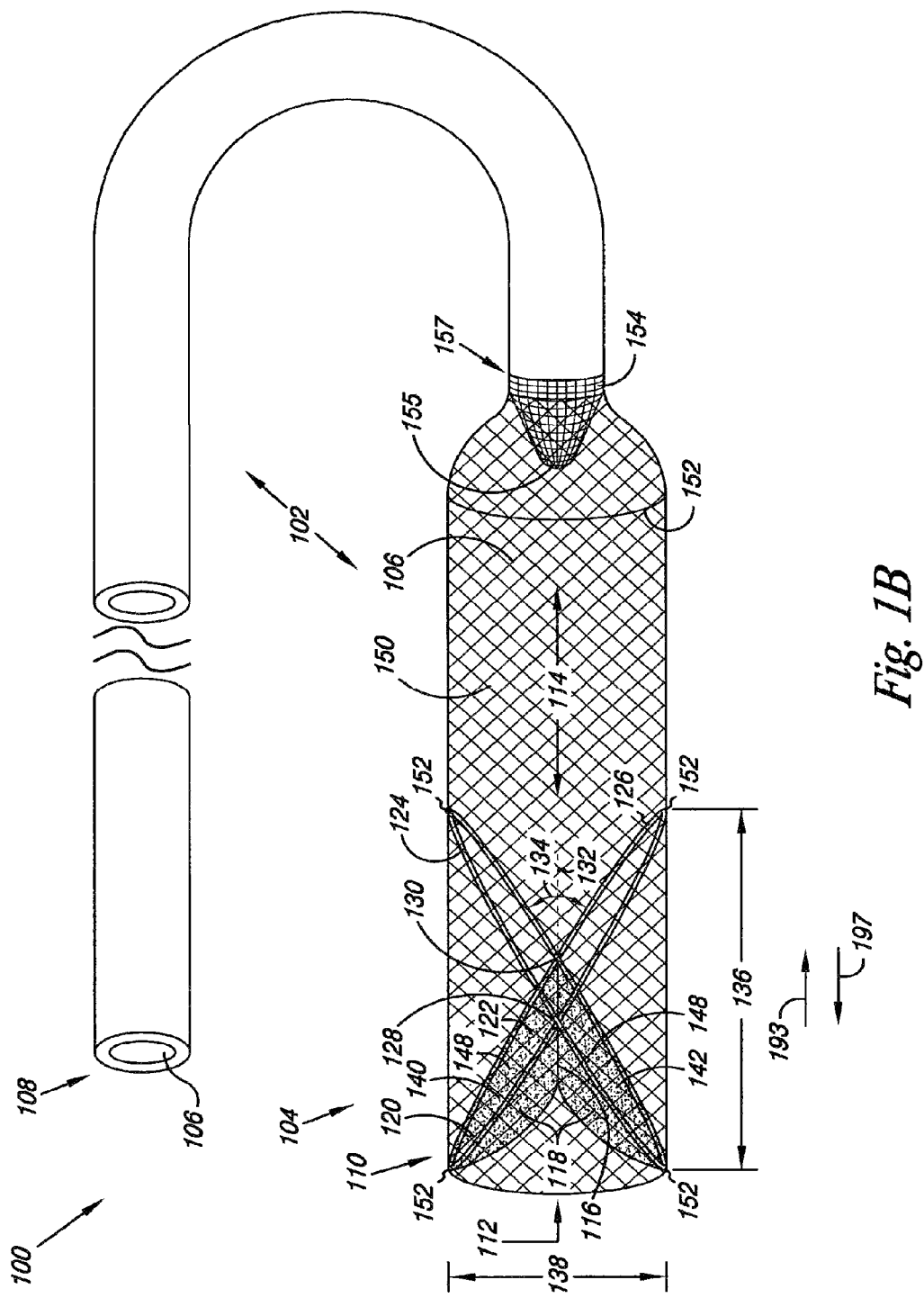

FIGS. 1A and 1B illustrate one embodiment of a filter system 100 shown in perspective view. Filter system 100 includes an elongate filter body 102 including an expandable filter region 150 and a valve 104. FIGS. 1A and 1B provide a perspective illustration of the valve 104 of filter system 100 in an open configuration (FIG. 1A) and a closed configuration (FIG. 1B). In addition, the perspectives illustrated in FIGS. 1A and 1B show the filter system 100 in an expanded configuration, as will be discussed herein.

In the present embodiments, the elongate filter body 102 defines a lumen 106 extending from a proximal end 108 towards a distal end 110. In one embodiment, the lumen 106 can be concentric with an elongate axis of the elongate filter body 102. The valve 104 also defines a lumen 112. In one example, the valve 104 can be adjoined proximal the distal end 110 of the elongate filter body, where the lumen 112 of the valve 104 and the lumen 106 of the elongate filter body 102 can form a single lumen 114. In other words, the lumens 106 and 112 can be contiguous so as to form the single lumen 114. Other configurations are also possible.

In the various embodiments, filter system 100 allows for both unidirectional flow of fluid and filtering of the fluid passing through the lumens 106 and 112. With respect to providing unidirectional flow of the fluid through lumens 106 and 112, the valve 104 includes a reversibly sealable opening 116. In one embodiment, the reversibly sealable opening 116 can be formed by one or more valve leaflets 118. In forming the reversibly sealable opening 116, the valve leaflets 118 are configured to move between an open configuration (e.g., FIG. 1A, allowing fluid to flow in a first direction 193 through the lumens 106 and 112) and a closed configuration (e.g., FIG. 1B, preventing fluid from flowing in a second direction 197 opposite the first direction 193).

The valve 104 can include any number of configurations so as to define the lumen 112 and provide the reversibly sealable opening 116 for unidirectional flow of the fluid through the lumen 112. For example, the valve 104 can include a frame 120 that supports a cover 122. In the various embodiments, the cover 122 defines the reversibly sealable valve leaflets 118 that provide for the unidirectional flow of a fluid through the lumen 112 of the valve 104.

Examples of a valve suitable for use as valve 104 is illustrated in U.S. patent application Ser. No. 10/741,995, entitled "Venous Valve Apparatus, System, and Method", and in U.S. patent application Ser. No. 11/052,655, entitled "Venous Valve Apparatus, System, and Method", both of which are hereby incorporated by reference in their entirety. As illustrated, frame 120 includes a variety of structural configurations. Generally, the frame 120 has a curved structural configuration, as will be discussed herein. For example, the frame 120 can include a first elliptical member 124 and a second elliptical member 126, as illustrated in FIGS. 1A and 1B.

In the various embodiments, the first elliptical member 124 and the second elliptical member 126 meet at a first region 128 and a second region 130, where the first region 128 and the second region 130 are opposite each other across axis 132. The first region 128 and the second region 130 can be located at any number of locations along the first elliptical member 124 and the second elliptical member 126. For example, the first region 128 and the second region 130 can be at or near a minor axis of the first elliptical member 124 and the second elliptical member 126. In an additional embodiment, the first region 128 and the second region 130 can be positioned away from the minor axis of the first elliptical member 124 and the second elliptical member 126.

While the term elliptical member is used herein, other shapes are possible for the structural members that help to form a valve according to the embodiments herein. For example, the frame 120 can include circular members that meet at the first region 128 and the second region 130. Other shapes besides elliptical and circular are also possible.

The first elliptical member 124 and the second elliptical member 126 meet at the first region 128 and the second region 130 at an angle 134. In one embodiment, the size of angle 134 when the valve 104 is expanded can be selected based upon the type of body lumen and the body lumen size in which the valve 104 is to be placed. Additional factors include, but are not limited to, a longitudinal length 136 and a width 138 of the valve 104. These factors, along with others discussed herein, can be used to provide the angle 134 that is sufficient to ensure that the first elliptical member 124 and the second elliptical member 126 have an appropriate expansion force against an inner wall of the body lumen in which the valve 104 is being placed.

The valve 104 also includes a flexible joint at and/or around axis 132 that allows the valve 104 to accommodate changes in body lumen size (e.g., diameter of the body lumen) by increasing or decreasing angle 134 when the valve 104 is expanded. In addition, the frame 120 also has the ability to flex, as discussed herein, to allow for the distance between the first region 128 and the second region 130 to increase or decrease, thereby further accommodating changes in the body lumen size (e.g., diameter of the body lumen). The frame 120 also provides sufficient contact and expansion force with the surface of a body lumen wall to encourage seating of the valve 104 and to prevent retrograde flow, i.e., second direction 197, within the body lumen.

The frame 120 can be formed from a biocompatible metal, metal alloy, polymeric material, or combinations thereof, which allow the frame 120 to move radially between the collapsed and expanded state, as discussed herein. To accomplish this, the biocompatible metal, metal alloy, or polymeric material should exhibit a low elastic modulus and a high yield stress for large elastic strains that can recover from elastic deformations. Examples of suitable materials include, but are not limited to, medical grade stainless steel (e.g., 316L), titanium, tantalum, platinum alloys, niobium alloys, cobalt alloys, alginate, or combinations thereof. In an additional embodiment, the frame 120 may be formed from a shape-memory material. Examples of a suitable shape-memory material include, but are not limited to, alloys of nickel and titanium in specific proportions known in the art as nitinol. Other materials are also possible.

The valve 104 can further include one or more radiopaque markers 152 (e.g., tabs, sleeves, welds). For example, one or more portions of the frame 120 can be formed from a radiopaque material. Radiopaque markers can be attached to and/or coated onto one or more locations along the frame 120. Examples of radiopaque materials include, but are not limited to, gold, tantalum, and platinum. The position of the one or more radiopaque markers can be selected so as to provide information on the position, location and orientation of the valve 104 during its implantation.

The valve 104 further includes the cover 122. In the various embodiments, the cover 122 forms the valve leaflets 118 joined to valve frame 120. The valve leaflets 118 can deflect between a closed configuration (FIG. 1B) in which retrograde fluid flow through the valve 104 is restricted, and an open configuration (FIG. 1A) in which antegrade fluid flow through the valve 104 is permitted. In one embodiment, valve leaflets 118 of the valve are configured to open and close in response to the fluid motion and/or pressure differential across the valve leaflets 118.

The example of valve 104 shown in FIGS. 1A and 1B provide embodiments in which the surfaces defining the reversibly sealable opening 116 include a first leaflet 140 and a second leaflet 142 coupled to the valve frame 120 to provide a two-leaflet configuration (i.e., a bicuspid valve) for valve 104. Although the embodiments illustrated in FIGS. 1A-1B of the present invention show and describe a two-leaflet configuration for valve 104, designs employing a different number of valve leaflets (e.g., tricuspid valve) are possible and considered within the scope of the embodiments.

The valve leaflets 118 can have a variety of sizes and shapes. For example, each of the valve leaflets 118 (e.g., first leaflet 140 and second leaflet 142) can have a similar size and shape. In an additional example, each of the valve leaflets 118 need not have valve leaflets 118 that are of a similar size and shape (i.e., the valve leaflets can have a different size and shape).

Valve frame 120 can include an open frame construction (i.e., valve frame 120 defines an opening) through which valve leaflets 118 can radially-collapse and radially-expand. The valve leaflets 118 can be provided over the open frame construction of the valve frame 120 to direct fluid flow through reversibly sealable opening 116 under specific fluid flow conditions. In one embodiment, the material of the valve leaflets 118 coupled to the valve frame 120 can be sufficiently thin and pliable so as to permit radially-collapsing of the valve leaflets 118 for delivery by catheter to a location within a body lumen.

In one embodiment, each of the valve leaflets 118 includes sufficient excess material spanning valve frame 120 such that fluid pressure (e.g., antegrade flow) acting on the valve leaflets 118 forces the valve 104 into an open configuration (FIG. 1A). Valve leaflets 118 can further include arcuate edges 144 and 146, as shown in FIG. 1A, that are positioned adjacent each other along a substantially catenary curve between the first region 128 and the second region 130 in the closed configuration (FIG. 1B) of valve 104. Similarly, arcuate edges 144 and 146 can help to define lumen 112 when the valve 104 is in the open configuration (FIG. 1A).

In an additional embodiment, in the open configuration the sufficient excess material spanning the valve frame 120 can allow the valve leaflets 118 to take on a semi-tubular structure, as shown in FIG. 1A, when fluid pressure opens the valve 104. In an additional embodiment, arcuate edge 144 and 146 of valve 100 can open to approximately the full inner diameter of body lumen.

Each of the valve leaflets 118 can further include a curve imparted thereto so as to provide a concave structure 148 to the leaflet 118. The concave structure 148 allows the valve leaflets 118 to better collect retrograde fluid flow to urge valve leaflets 118 towards the closed configuration. For example, as retrograde flow begins, the valve leaflets 118 respond by moving towards the center of valve 104. As the valve leaflets 118 approach the center of the device the valve leaflets 118 make sufficient contact to effectively close the reversibly sealable opening 116 of valve 104 and thereby restrict retrograde fluid flow.

In an additional embodiment, the valve leaflets 118 can include one or more support structures. For example, the valve leaflets 118 can include one or more support ribs having a predetermined shape. In one embodiment, the predetermined shape of the support ribs can include a curved bias so as to provide the valve leaflets 118 with a curved configuration. Support ribs can be constructed of a flexible material and have dimensions (e.g., thickness, width and length) and cross-sectional shape that allows the support ribs to be flexible when valve leaflets 118 are urged into an open position, and stiff when the valve leaflets 118 are urged into a closed position upon experiencing sufficient back flow pressure from the direction downstream from the valve. In an additional embodiment, support ribs can also be attached to valve frame 120 so as to impart a spring bias to the valve leaflets in either the open or the closed configuration.

The valve leaflets 118 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene, polyurethane, segmented poly(carbonate-urethane), Dacron, polyethlyene (PE), polyethylene terephthalate (PET), silk, urethane, Rayon, Silicone, or the like. Possible biologic materials include, but are not limited to allogeneic or xenograft material. These include explanted veins and decellularized basement membrane materials, such as small intestine submucosa (SIS) or umbilical vein.

Valve leaflets 118 can be coupled to the various embodiments of valve frame 120, as described herein, in any number of ways. For example, a variety of fasteners can be used to couple the material of the valve leaflets 118 to the valve frame 120. Fasteners can include, but are not limited to, biocompatible staples, glues, and sutures. In one embodiment, the material of the valve leaflets 118 can be wrapped at least partially around the valve frame 120 and coupled using the fastener. In an additional embodiment, valve leaflets 118 can be coupled to the various embodiments of valve frame 120 through the use of heat sealing, solvent bonding, adhesive bonding, or welding the valve leaflets 118 to either a portion of the valve leaflet 118 (i.e., itself) and/or the valve frame 120. Valve leaflets 118 can also be attached to valve frame 120 according to the methods described in U.S. Patent Application Publication US 2002/0178570 to Sogard et al., which is hereby incorporated by reference in its entirety.

In an alternative embodiment, the valve 104 can include three leaflets, with the various frames and covering configurations as described herein. Further, valve 104 can be configured to extend proximally and distally in a curvilinear manner to accommodate the coronary ostia and the diseased valve. For example, leaflets can extend past the coronary ostia in the central portion of the leaflets, and extend to accommodate the attachment points of the diseased valve by incorporating a tri-lobar saddle shaped configuration. In one embodiment, the valve 104 can include a configuration that allows the valve 104 to be place functionally distal to the coronary ostia for proper coronary perfusion, while maintaining sufficient clearance for the diseased valve and the repair or replacement of the diseased valve to be performed. Examples of a three leaflet valve suitable for use as valve 104 are illustrated in U.S. patent application Ser. No. 11/107,162, entitled "Valve Apparatus, System and Method", and U.S. patent application Ser. No. 10/933,088, entitled "Cardiac Valve, System, and Method", which is hereby incorporated by reference in its entirety.

In various embodiments, a portion of the elongate filter body 102 can include an expandable filter region 150 to filter the unidirectional flow of the fluid moving through the valve 104. As used herein, filtering of fluid can be accomplished through use of the expandable filter region 150 by trapping and/or inhibiting the passage of particular matter released into and/or present in the fluid moving through the valve 104. Trapped particulate matter can then be removed with the filter system 100 through the lumen 106.

As illustrated in FIGS. 1A-1B, the valve 104 can be adjoined proximal the distal end 110 of the elongate filter body 102. For example, the frame 120 of the valve 104 can be coupled to the expandable filter region 150 proximal the distal end 110 of the elongate filter body 102. Methods of coupling the frame 120 to the expandable filter region 150 of the elongate filter body 102 can be as described herein for coupling the valve leaflets 118 to the frame 120.

As will be illustrated herein, the expandable filter region 150 can move between a first configuration (e.g., a compressed state, shown in FIG. 3A) and a second configuration (e.g., an expanded state, shown in FIGS. 1A-1B and FIGS. 2A-2B). In one embodiment, the expandable filter region 150 can expand from the first configuration to the second configuration due to force imparted by the frame 120 as it expands. In addition, the expandable filter region 150 can expand from the first configuration to the second configuration by a combination of force imparted by the frame 120 as it expands and under pressure of the unidirectional flow of the fluid. Additionally, the force imparted by the frame when the valve is in the open configuration can help to maintain the expandable filter region expanded when under retrograde fluid flow, such as when the valve is in a closed configuration. In an additional embodiment, the expandable filter region 150 can be configured to radially self-expand when released from a compressed state.

In the various embodiments, the expandable filter region 150 in its deployed state can fill the cross-section area of the lumen in which the expandable filter region 150 and valve 104 are deployed. In addition, filter region 150 in its deployed state can apply sufficient pressure to the inner wall of the lumen to reduce the volume of fluid (e.g., blood) that may pass between the filter region 150 and the surface of the lumen wall. In one embodiment, the valve frame 120 can be used at least in part to apply the sufficient pressure to the inner wall of the body lumen. As will be appreciated, the area and shape defined by the expandable filter region 150 (e.g., the diameter of the expandable filter region) in its deployed state can be dependent upon the location in which the apparatus is intended to be used.

Examples of expandable filter region 150 include those having a woven, braided and/or a knit configuration as the same will be known and understood by one of ordinary skill in the art. Alternatively, the expandable filter regions 150 can be formed of a material having pores formed therein or imparted thereto. In the various embodiments, the expandable filter regions 150 can be formed of a number of materials. Materials can include polymers, such as ePTFE, PTFE, polystyrene-polyisobutylene-polystyrene, polyurethane, segmented poly(carbonate-urethane), Dacron, PE, PET, silk, urethane, Rayon, Silicone, polyamid, mixtures, and block co-polymers thereof.

In one embodiment, expandable filter region 150 can be configured to reduce passage of potentially injurious emboli to arteries feeding the brain, heart, kidneys, and other tissues and organs. For example, expandable filter region 150 can help to reduce or prevent passage of emboli greater than about 5 to 1000 micrometers in cross-sectional size. Expandable filter region 150 may also prevent passage of emboli larger than 50 to 200 micrometers in cross-sectional size. Multiple regions or layers of expandable filter region 150 may be incorporated to more efficiently filter emboli, such as a 200 micrometer portion of the expandable filter region 150 to capture larger particles and a 75 micrometer portion of the expandable filter region 150 to capture smaller particles.

Additional examples of the expandable filter region 150 include the radially self-expanding configurations formed from temperature-sensitive memory alloy which changes shape at a designated temperature or temperature range. Examples of such materials include, but are not limited to, nitinol and nitinol-type metal alloys. Alternatively, self-expanding configurations for the expandable filter region 150 include those having a spring-bias imparted into the members forming the filter region 150. The expandable filter region 150 can have a woven, braided and/or a knit configuration that can also impart a self-expanding aspect to the expandable filter region 150.

In an additional embodiment, the filter region 150 can further include radiopaque markers 152. For example, radiopaque markers (e.g., attached or coated) can be used to mark the location of the valve 104 and/or the expandable filter region 150. Other portions of filter system 100 can also be marked with radiopaque markers as necessary to allow for visualization of the location and position of parts of the filter system 100.

The elongate filter body 102 can further include a fluid tight plug 154 positioned within the lumen 106 of the elongate filter body 102. In one embodiment, the fluid tight plug 154 can be positioned proximal the expandable filter region 150 so as to occlude the lumen 106, thereby directing the unidirectional flow of the fluid from the lumen 106 through the expandable filter region 150.

The fluid tight plug 154 can have a variety of shapes and configurations. For example, a first end 155 and a second end 157 of the fluid tight plug 154 can include a flat planar surface. In an alternative embodiment, the first end 155 of the fluid tight plug can include a conical configuration, as shown in FIGS. 1A and 1B. Other shapes and configurations for the fluid tight plug 154 are also possible.

FIGS. 2A and 2B illustrate an additional embodiment of a filter system 200. FIGS. 2A and 2B provide a perspective illustration of the filter system 200 that includes both the elongate filter body 202, as described herein, and the valve 204. In the present example, however, the valve 204 includes a frame 220 and a cover 222, including valve leaflets 240 and 242 (shown in FIG. 2A), having a different configuration as compared to the valve 104 described above in FIGS. 1A and 1B. One example of valve 204 is illustrated in U.S. patent application Ser. No. 10/741,992, entitled "Venous Valve Apparatus, System, and Method", which is hereby incorporated by reference in its entirety.

The frame 220 of valve 204 includes an outer surface 256 and an inner surface 258 opposite the outer surface 256. The inner surface 258 defines the lumen 212 of the valve 204 for passing fluid therethrough. The frame 220 also includes a first end 262 and a second end 260. In one embodiment, the cover 222 can be located over at least the outer surface 256 of the frame 220. For example, the cover 222 can extend around a perimeter of the frame 220 so as to completely cover the outer surface 256 of the frame 220. In other words, the cover 222 extends over the outer surface of the frame 220 so that there are no exposed portions of the outer surface 256 of the frame 220. In an additional embodiment, the cover 222 can also be located over at least the inner surface 258 of the frame 220. A further embodiment includes the cover 222 located over at least the outer surface 256 and the inner surface 258.

In one embodiment, the frame 220 can include an open frame configuration that includes a first vertex 263 and a second vertex 264 relative the second end 260 of the frame 220. Frame 220 can further include a first valley 266 and a second valley 268 adjacent the second end 260 relative the first vertex 263 and the second vertex 264. As illustrated in FIGS. 2A and 2B, the first vertex 263 and the second vertex 264 can be positioned opposite each other along a common axis 270 (shown in FIG. 2B). FIGS. 2A and 2B also illustrate that the first valley 266 and the second valley 268 can be positioned opposite each other and perpendicular to axis 270. Other relative positions for the first and second vertex 263 and 264, and the first and second valley 266 and 268 are also possible. As one of ordinary skill will understand, more than two vertexes and valleys may be included in the embodiments. For example, where an embodiment includes three valve leaflets, e.g., a tricuspid valve, three vertexes and three valleys can also be included to help form the three leaflets.

The cover 222 can further include valve leaflets 240 and 242 that define the reversibly sealable opening 216 for the unidirectional flow of the fluid through the lumen 212. For example, the surfaces of the cover 222 can be deflectable between a closed configuration (FIG. 2B) in which fluid flow through the lumen 212 can be restricted and an open configuration (FIG. 2A) in which fluid flow through the lumen 212 can be permitted in response to the fluid motion and/or pressure differential across the valve leaflets 240 and 242.

The example of valve 204 shown in FIGS. 2A and 2B provide embodiments in which the surfaces defining the reversibly sealable opening 216 include the first leaflet 240 and the second leaflet 242 coupled to the valve frame 220 to provide a two-leaflet configuration (i.e., a bicuspid valve) for valve 204. Although the embodiments illustrated in FIGS. 2A and 2B of the present invention show and describe a two-leaflet configuration for valve 204, designs employing a different number of valve leaflets (e.g., tricuspid valve) are also possible.

In one embodiment, each of the valve leaflets 240 and 242 include sufficient excess material spanning valve frame 220 such that fluid pressure (e.g., antegrade flow) acting on the valve leaflets 240 and 242 forces the valve 204 into an open configuration (FIG. 2A). Valve leaflets 240 and 242 further include arcuate edges, as illustrated in FIGS. 1A and 1B and shown as 144 and 146, that are positioned adjacent each other along a substantially catenary curve between the first vertex 263 and the second vertex 264 in the closed configuration (Figure B) of valve 204. Similarly, arcuate edges 244 and 246 can help to define lumen 212 when the valve 204 is in the open configuration (FIG. 2A).

In an additional embodiment, in the open configuration the sufficient excess material spanning the valve frame 220 between the first vertex 263 and the second vertex 264 can allow the valve leaflets 240 and 242 to take on a semi-tubular structure, as shown in FIG. 2A, when fluid pressure opens the valve 204. In an additional embodiment, arcuate edge 244 and 246 of valve 204 can open to approximately the full inner diameter of body lumen.

Each of the valve leaflets 240 and 242 can further include a curve imparted thereto so as to provide a concave structure to the leaflet 240 and 242. The concave structure allows the valve leaflets 240 and 242 to better collect retrograde fluid flow to urge valve leaflets 240 and 242 towards the closed configuration (FIG. 2B). For example, as retrograde flow begins, the valve leaflets 240 and 242 respond by moving towards the center of valve 204. As the valve leaflets 240 and 242 approach the center of the device the valve leaflets 240 and 242 can make sufficient contact to effectively close the reversibly sealable opening 116 of valve 104 and thereby restrict retrograde fluid flow, i.e., second direction 197 as shown in FIGS. 1A and 1B.

Figure 3A:
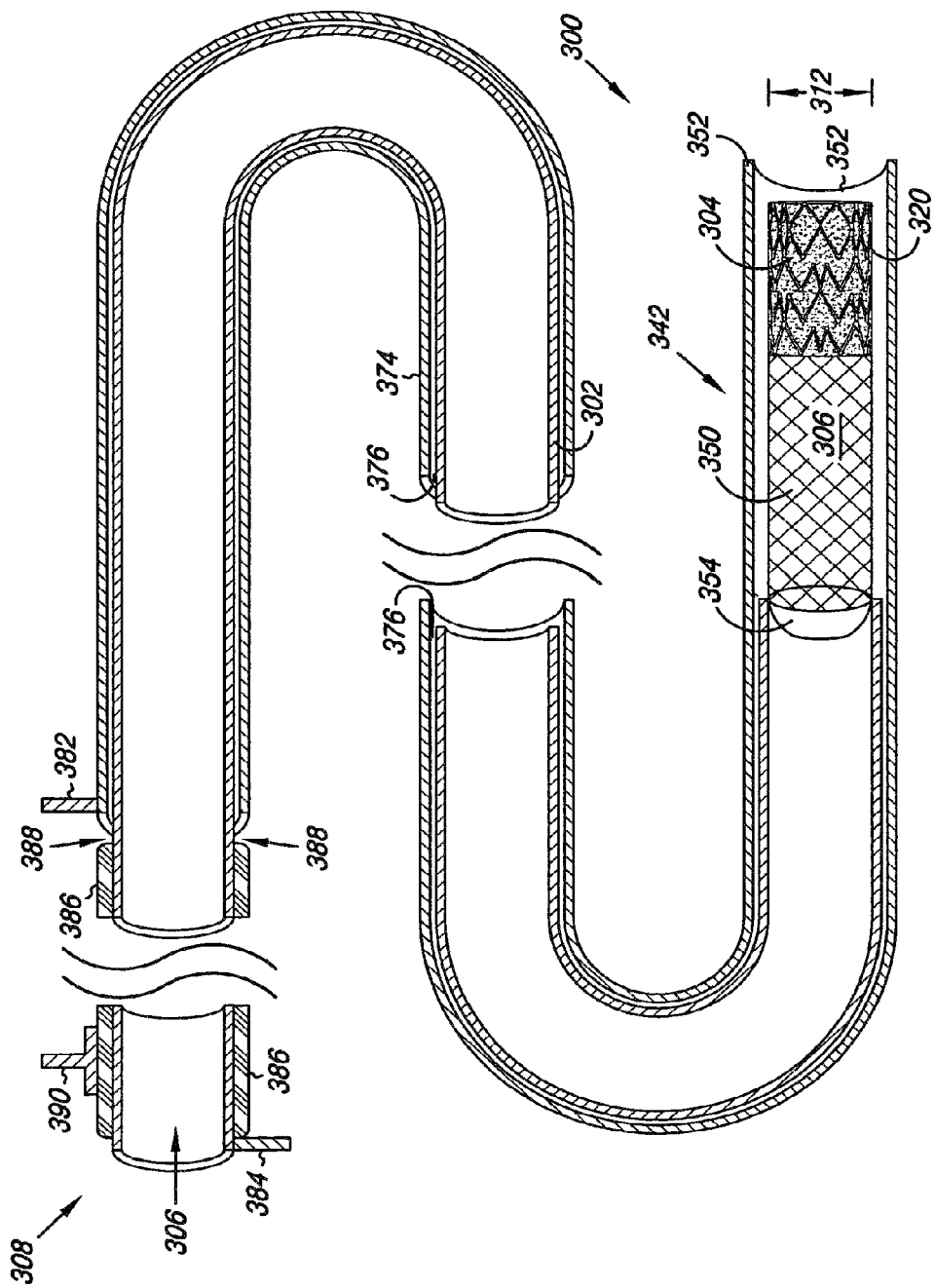
FIGS. 3A-3C illustrate another embodiment of the filter system.
Figure 3B:
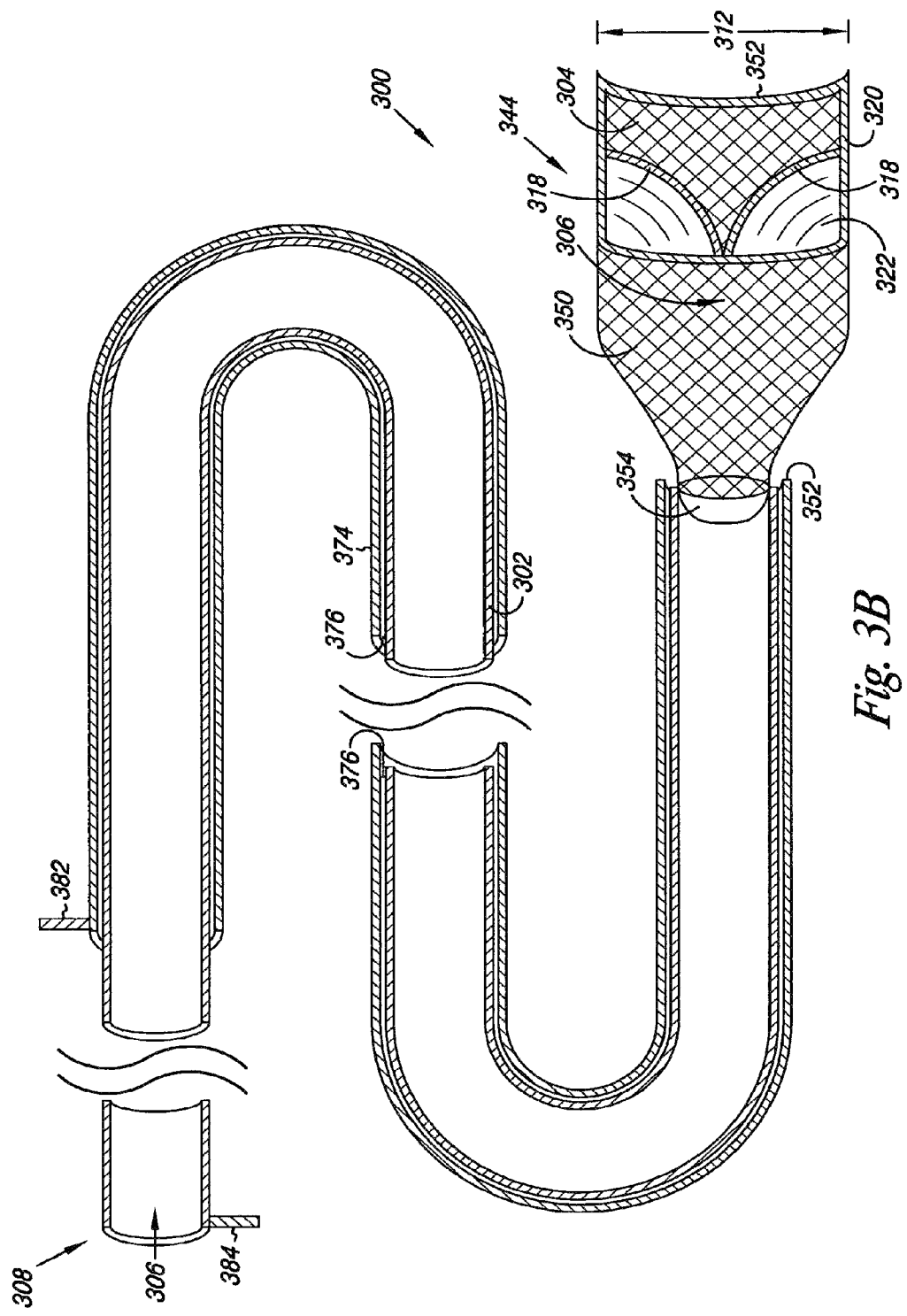

FIGS. 3A and 3B provide a further illustration of the filter system 300 (i.e., the elongate filter body 302, valve 304, and filter region 350) that includes a sheath 374 having a lumen 376. FIGS. 3A and 3B provide a sectional illustration of the filter system 300 at least partially contained within a lumen 376 of the sheath 374 (FIG. 3A) and of the filter system 300 at least partially deployed from the lumen 376 of the sheath 374 (FIG. 3B).

In various embodiments, both the valve 304 and the filter region 350 of the elongate filter body 302 can be releasably positioned in a coaxial arrangement within the lumen 376 of the sheath 374. As discussed herein, the configuration of the support frame 320 provides the valve 304 with sufficient flexibility to move between the first configuration 342 (e.g., a refracted state within the lumen 376 of the sheath 374 as shown in FIG. 3A) and the second configuration 344 (e.g., an extended state outside the lumen 376 of the sheath 374 as shown in Figures FIG. 3B).

In one embodiment, the valve 304 can be configured to reside in the compressed state when retracted within the lumen 376 of the sheath 374, as illustrated in FIG. 3A, and in an expanded state when extended from the lumen 376 of the sheath 374, as illustrated in FIG. 3B. In one embodiment, the valve 304 expands from its compressed state within the lumen 376 to the deployed state when the sheath 374 is retracted from around the valve 304.

The sheath 374 can be formed of a number of materials. Materials include polymers, such as PVC, PE, POC, PET, polyamid, mixtures, and block co-polymers thereof. In addition, the sheath 374 can have a wall thickness and an inner diameter sufficient to maintain both the valve 304 and the expandable filter region 350 in the retracted state when they are positioned within the lumen 376. In an additional embodiment, the sheath 374 can further include radiopaque markers 352. For example, radiopaque markers (e.g., attached or coated) can be used to mark the location and allow for visualization of the location and position of parts of the sheath 374.

In the various embodiments, the support frame 320 of the cardiac valve 304 expands to increase the diameter 312 of the lumen 306 of the valve 304 as the valve 304 is extended from the sheath 374. In one embodiment, the diameter 312 of the lumen 306 can be determined based upon the type of body lumen and the body lumen size in which the valve 304 is to be placed. In an additional example, there can also be a minimum value for the width for the support frame 320 that ensures that the valve 304 will have an appropriate expansion force against the inner wall of the body lumen to prevent retrograde flow within the body lumen.

In addition, the lumen 306 of the elongate filter body 302 in the filter region 350 also increases in diameter as the valve 304 and the elongate filter body 302 are extended from the sheath 374. In one embodiment, the expandable filter region 350 can expand from the first configuration to the second configuration due in part to force imparted by the frame 320 as it expands and under pressure of the unidirectional flow of the fluid. In an additional embodiment, the expandable filter region 350 can be configured to radially self-expand, as the same has been described herein, when released from its compressed state within the lumen 376 of the sheath 374.

The expandable filter region 350 in its deployed state can fill the cross-section area of a body lumen in which the valve 304 and expandable filter region 350 are deployed. In addition, filter region 350 in its deployed state can apply sufficient pressure to the inner wall of the body lumen to reduce the volume of fluid (e.g., blood) that may pass between the filter region 350 and the surface of the body lumen wall. As will be appreciated, the area and shape defined by the expandable filter region 350 (e.g., the diameter of the expandable filter) in its deployed state will be dependent upon the location in which the filter system is intended to be used.

The filter system 300 can be extended and retracted from the lumen 376 of the sheath 374 in any number of ways. For example, the elongate filter body 302 can be pulled longitudinally within the lumen 376 of the sheath 374 so as to retract the valve 304 and the filter region 350 of the elongate filter body 302. In this embodiment, the elongate filter body 302, supported by the sheath 374, provides sufficient column strength to allow force imparted at the proximal end 308 of the elongate filter body 302 to retract the valve 304 and the filter region 350.

In an additional embodiment, a portion of the elongate filter body 302 extending from the filter region 350 to the proximal end 308 can be reinforced and/or have an alternative construction relative the filter region 350 so as to impart sufficient column strength to the elongate filter body 302. The elongate filter body 302 can then be pushed longitudinally within the lumen 376 of the sheath 374 so as to extend the valve 304 and the filter region 350 of the elongate filter body 302.

In an additional embodiment, the valve 304 and the filter region 350 can be deployed and retracted by moving the sheath 374 relative the elongate filter body 302. In this embodiment, the elongate filter body 302 can be held while the sheath 374 is moved longitudinally so as to either deploy or retract the valve 304 and the filter region 350.

The filter system 300 and the sheath 374 can further include handles positioned at the proximal end 308 of the elongate filter body 302 and a first sheath end 378 of the sheath 374. In one embodiment, the sheath 374 includes a handle 382 and the elongate filter body 302 includes a handle 384. Handles 382 and 384 allow the sheath 374 and the elongate filter body 302 to move relative to each other so as to extend and/or retract the valve and a portion of the elongate filter body from the lumen 376 of the sheath 374. In one embodiment, the distance between the handles 382 and 384 can correspond approximately to the length of the compacted valve 304 and the filter region 350 to effectively deploy the expandable filter region 350 and valve 304. Other configurations and relational lengths are possible.

In an additional embodiment, filter system 300 and the sheath 374 can further include a sleeve 386 having a slit 388 and a pull tab 390 positioned between the handles during delivery to prevent inadvertent exposure of the valve 304 and filter region 350. For example, the sleeve 386 can be stripped from the filter system 300 by pulling the pull tab once the sheath 374 has been placed at the predetermined location at which the valve 304 and the filter region 350 are to be deployed. Other removable structures for preventing inadvertent exposure of the valve 304 and filter region 350 are also possible.

Figure 3C:
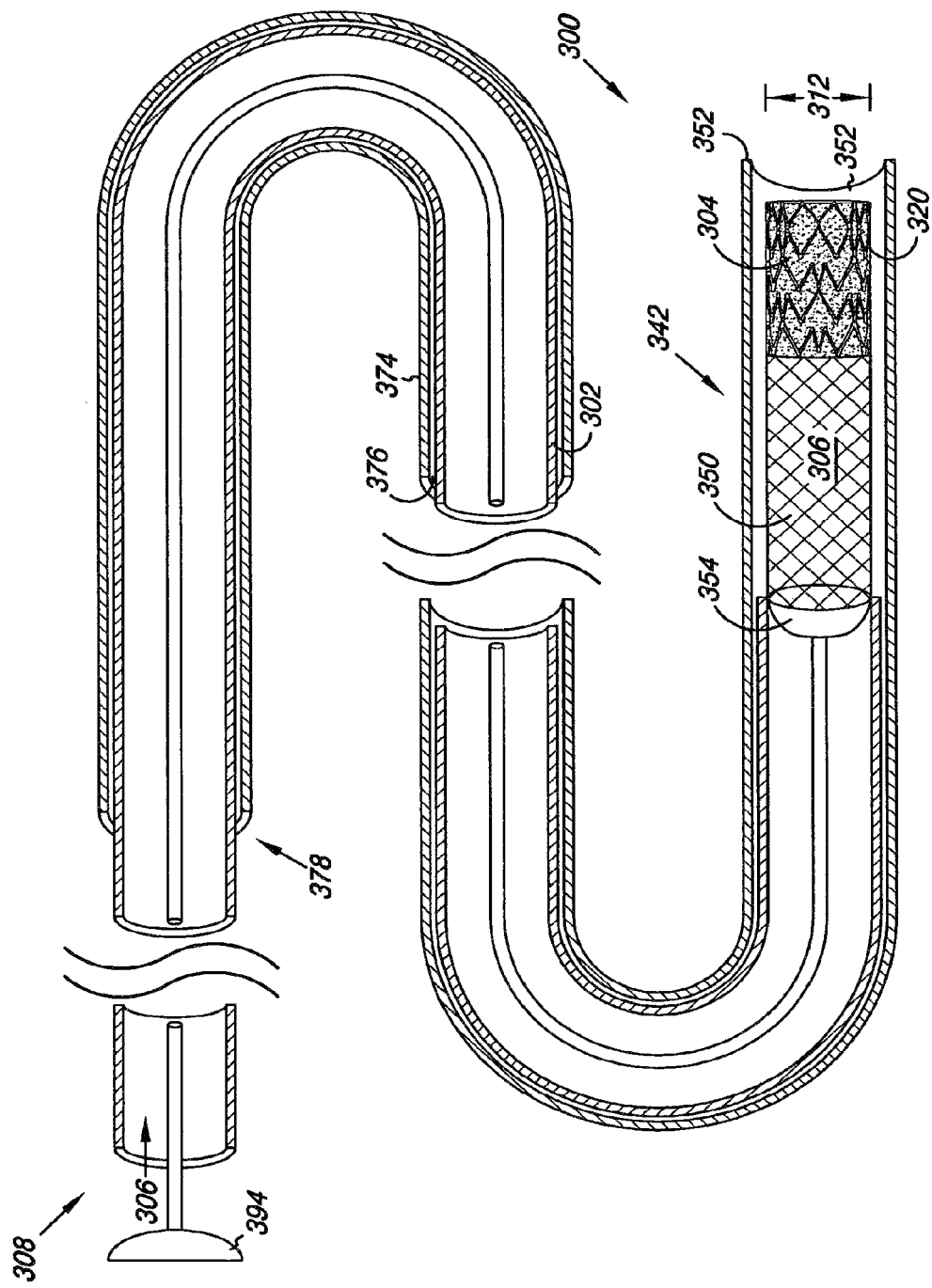

In an additional embodiment, the filter system 300, as shown in FIG. 3C can be extended and/or retracted from the sheath 374 through the use of a deployment rod 394. In one embodiment, the deployment rod 394 extends from the proximal end 308 of the elongate filter body 302 through the lumen 376 to the fluid tight plug 354, as the same has been described in connection with FIGS. 1A and 1B. In one embodiment, the deployment rod 394 can be used to move the elongate filter body 302 and the valve 304 relative the sheath 374.

For example, the deployment rod 394 can extend through the lumen 312 to the fluid tight plug 354, where the deployment rod 394 can be used to push the filter system 300 relative the sheath 374 to deploy the valve 304 and the filter region 350 and/or pull the filter system 300 relative the sheath 374 to draw the valve 304 and the filter region 350 back into its compressed state within the lumen 376 of the sheath 374. Alternatively, the deployment rod 394 can be used to change the position of the valve 304 and filter region 350 once deployed from a first position within the lumen to a second position.

In the various embodiments, the deployment rod 394 and the fluid tight plug 354 can further include releasably interconnecting members to allow the deployment rod 394 and the fluid tight plug 354 to be separated. For example, the fluid tight plug 354 can include a socket having threads to receive and interact with a threaded portion of the deployment rod 394. This structure allows for the deployment rod 394 to be inserted through the lumen 376 of the elongate filter body 302 to the fluid tight plug 354, where the treaded portion of the deployment rod 394 can be screwed into the threaded socket of the fluid tight plug 354. The deployment rod 394 can then be removed from the lumen 376 by unscrewing the threaded portion of the deployment rod 394 from the threaded socket of the fluid tight plug 354. As will be appreciated, other ways of decoupling the deployment rod 394 and the fluid tight plug 354 are also possible.

In one embodiment, the deployment rod 394 can be formed of a number of materials. Materials include polymers, such as PVC, PE, POC, PET, polyamid, mixtures, and block co-polymers thereof. In addition, the deployment rod 394 can be formed of medical grade stainless steel (e.g., 316L), titanium, tantalum, platinum alloys, niobium alloys, cobalt alloys, alginate, or combinations thereof.

FIGS. 4A-4D provides a further illustration of the filter system 400 that includes the sheath 474, as previously discussed, and a catheter 401 and an apparatus 445. FIGS. 4A-4D provide perspective illustrations of the filter system 400 at least partially contained within the lumen 476 of the sheath 474, with the catheter 401 and the apparatus 445 at least partially contained within a lumen 406 of the elongate filter body 402.

Examples of the catheter 401 and the apparatus 445 are illustrated in U.S. patent application Ser. No. 11/049,000, entitled "Vascular Catheter, System, and Method", which is hereby incorporated by reference in its entirety. In the various embodiments, the catheter 401 includes an elongate body 403 having a first lumen 405 extending between a proximal end 407 and a distal end 409. In one embodiment, the first lumen 405 allows for additional elongate members to travel along a longitudinal axis of the elongate body 402.

The catheter 401 further includes a first cutting head 411 having a blade 413 and an elongate pulling member 415. The first cutting head 411 can be positioned adjacent the distal end 409 of the elongate body 403 of the catheter 401 with the elongate pulling member 415 extending through the first lumen 405. In one embodiment, the elongate pulling member 415 can slide within the first lumen 405 to move the first cutting head 411 relative the distal end 409 of the elongate body 403 of the catheter 401.

The catheter 401 also includes a second cutting head 417 having a blade 419. The second cutting head 417 can be positioned adjacent the distal end 409 of the elongate body 403 between the distal end 409 and the first cutting head 411. The blade 413 of the first cutting head 411 can move relative the blade 419 of the second cutting head 417 to provide a shearing action. In one example, the shearing action can be sufficient for cutting cardiac tissue.

Figure 4A:
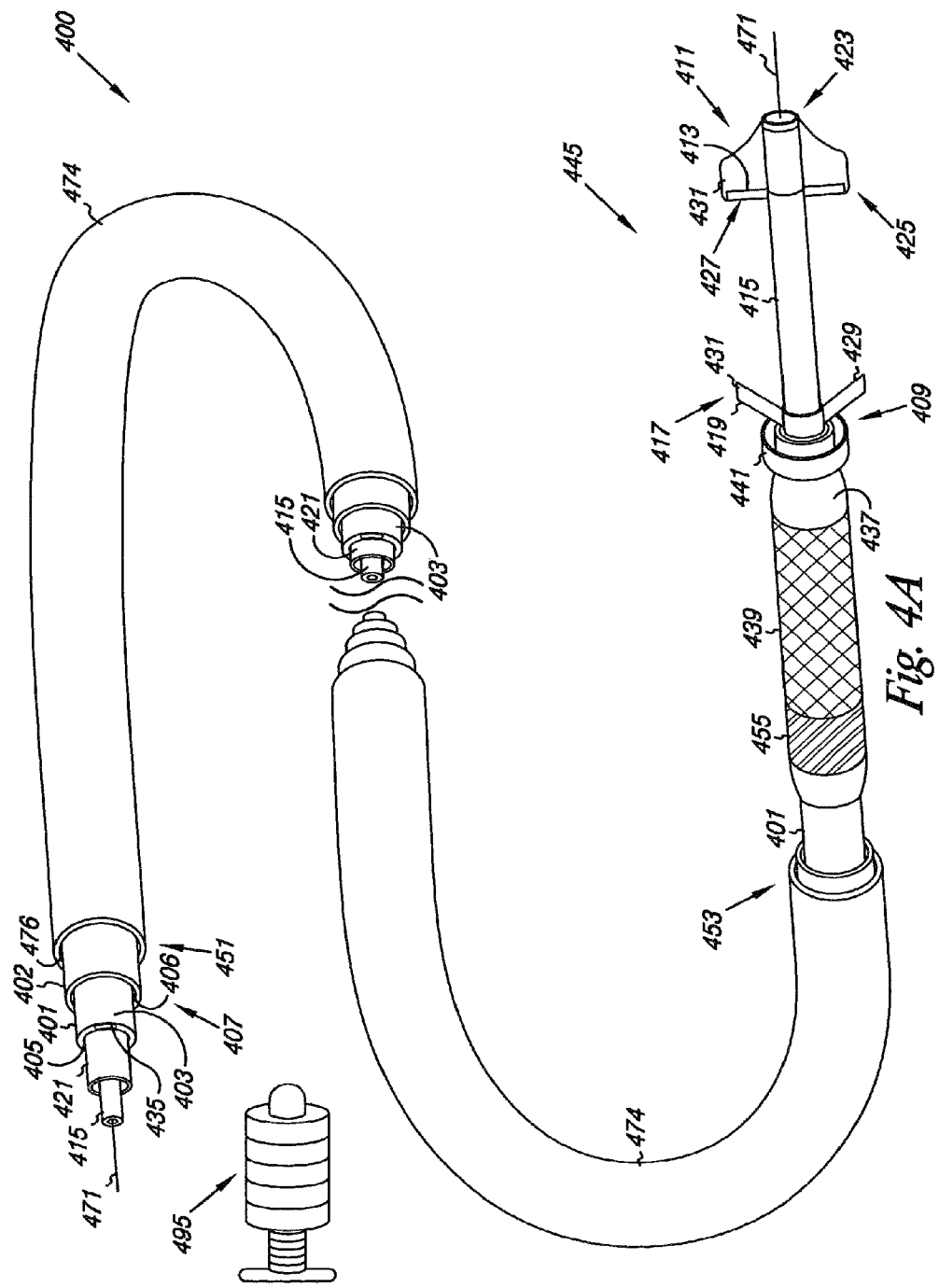
FIGS. 4A-4D illustrate another embodiment of the filter system.

FIG. 4A further illustrates an embodiment in which the second cutting head includes an elongate pushing member 421. In one embodiment, the elongate pushing member 421 can slide within the first lumen 405 to move the second cutting head 417 relative the distal end 409 of the elongate body 403 and the first cutting head 411. In one embodiment, the elongate pulling member 415 can be arranged concentrically with the elongate pushing member 421 in the first lumen 405.

As illustrated, the elongate pulling member 415, the elongate pushing member 421 and the first lumen 405 of the elongate body 403 can be positioned coaxially. In one embodiment, the lumen 405 has a diameter sufficient to accommodate the elongate pushing member 421. Similarly, the elongate pushing member 421 had a diameter sufficient to accommodate the elongate pulling member 415.

In addition, the elongate pulling member 415 and the elongate pushing member 421 can be structured such that their relative rotational movement is restricted. In other words, relative axial rotation of the elongate pulling member 415 and the elongate pushing member 421 is restricted due to the structure of the members 415 and 421. For example, this can be accomplished using one or more physical structures formed in and/or attached to the members 415 and 421.

In one embodiment, one of the members 415 or 421 can include a channel through which an extension from the other of the members 415 or 421 can travel so as to inhibit axial rotation of the members 415 and 421. Alternatively, the members 415 and 421 could have a cross-sectional shape that inhibits relative axial rotation. Examples of such cross-sectional shapes include oval or elliptical cross-sectional shapes. Other shapes are also possible.

In addition to providing a sufficient diameter, a gap can exist between the opposing surfaces of the first lumen 405 and the elongate pushing member 421 to allow the elongate pushing member 421 to move through the first lumen 405 from force applied at the proximal end of the elongate pushing member 421. Similarly, a gap can exist between the opposing surfaces of the elongate pushing member 421 and the elongate pulling member 415 to allow the elongate pushing member 421 and the elongate pulling member 415 to move relative each other from force applied at the proximal end of the elongate pushing member 421 and/or the elongate pulling member 415. The elongate pull member 415 can further include a lumen 471 for tracking over a guidewire. A lubricant can be included on the surfaces of the elongate pulling member 415, the elongate pushing member 421 and the first lumen 405.

The first cutting head 411 further includes a shape conducive to passing the catheter 401 and the filter system 400 through a body lumen (e.g., a lumen of the cardiovascular system). For example, the first cutting head 411 can include a conical shape having a first end 423 and a second end 425, where the first end 423 has a diameter that is less than a diameter of the second end 425. Other shapes are also possible. In addition, the shape of the first cutting head 411 can be configured to protectively house the blade 413 from structures passing by the first end 423 towards the second end 425. In other words, the shape of the first cutting head 411 can be used to shield the blade 413 from unintentionally interfering and/or cutting tissue within a body lumen.

In one embodiment, the blade 413 can be radially positioned relative the elongate pulling member 415 generally along the second end 425 of the first cutting head 411. As will be appreciated, the first cutting head 411 can include more than one blade 413. Each blade 413 and 419 further includes a cutting edge 427 and 429, respectively, in alignment so as to provide shearing action between a pair of the cutting edges 427 and 429 of the blades 413 and 419. For example, the first cutting head 411 can move relative the second cutting head 417 to allow the cutting edge 427 of the blade 413 of the first cutting head 411 to slide past the cutting edge 429 of the blade 417 of the second cutting head 417. Example of suitable materials for the blades 413 and 419 include, but are not limited to, stainless steel (e.g., 316L) and titanium.

In one embodiment, blades 413 and 419 can be secured to the first cutting head 411 and the second cutting head 417, respectively, in any number of ways. For example, blades 413 and 419 can be secured to the cutting heads 411 and 417 through the use of mechanical fasteners, such as screws, and/or interlocking pins and sockets. In addition, blades 413 and 419 can be secured to the cutting heads 411 and 417 through the use of chemical adhesives. Examples of such chemical adhesives include, but are not limited to, medical grade adhesives such as cyanoacrylate, acrylic, silicone, and urethane adhesives.

In an additional embodiment, the first cutting head 411 can be configured to receive and house at least a portion of the second cutting head 417, including the blade 419, such that the second blade 419 does not pass beyond the first cutting head 411. For example, the first cutting head can include a socket that extends radially relative the elongate pulling member 415 and distally from the blade 413 to receive the blade 419 of the second cutting head 417 as the blade 419 passes the blade 413. In one embodiment, the blade 419 can be positioned within the socket of the first cutting head 411 as the catheter 401 is moved through a lumen.

Catheter 401 can have various lengths between the proximal end 407 and the first cutting head 411. In one embodiment, the length between the proximal end 407 and the first cutting head 411 is sufficient to allow the catheter 401 to be percutaneously implanted through a patient's vasculature to position the cutting heads (e.g., the first and second cutting heads) at a predetermined location. Examples of the predetermined locations include, but are not limited to, cardiovascular locations such as on or adjacent to a cardiac valve of the heart (e.g., the aortic valve), including within a chamber of the patient's heart (e.g., the left ventricle of the heart). As will be appreciated, the length between the proximal end 407 and the first cutting head 411 will be dependent upon each patient's physiological structure and the predetermined location within the patient.

The elongate body 403 of the catheter 401, the elongate pulling member 415, the elongate pushing member 421, the second cutting head 417 and the first cutting head 411 can be formed from a wide variety of materials and in a wide variety of configurations. For example, the materials may include, but are not limited to, one or more of polyvinyl chloride (PVC), polyethylene (PE), polyolefin copolymer (POC), polyethylene terephthalate (PET), polyamid, mixtures, and block co-polymers thereof. Alternatively, the materials may include one or more alloys in any number of configurations. For example, the materials may include stainless steel (e.g., 316L), titanium, or other medical grade alloys as are known. These materials may also have a woven configuration or a solid extruded configuration.

The selection of material and configuration allows for the elongate body 403, the elongate pulling member 415, the elongate pushing member 421, the second cutting head 417 and the first cutting head 411 to each have the flexibility, and the ability to be either pushed and/or pulled thereby accomplishing the actions described for the components herein. As will be appreciated, selection of the material can be based generally on a broad range of technical properties, including, but not limited to, modulus of elasticity, flexural modulus, and Shore A hardness required for the embodiments of the present invention. Components of the present apparatus and/or system can also be coated for lubrication, for abrasion resistance, or to deliver an anticoagulatory drug.

As an alternative configuration, the cutting mechanism of first cutting head 411 and second cutting head 417 can be accomplished by alternate cutting, shearing, slicing, grinding or ablative means as are known for other purposes. For example, thermal energy can be used to weaken or slice the diseased valve, rolling cutters could be incorporated, or a "cutting balloon" mechanism could be incorporated.

In an additional embodiment, the catheter 401 can further include radiopaque markers 431. For example, radiopaque markers (e.g., attached or coated) can be used to mark the location of the first cutting head 411 and the second cutting head 417. In addition, radiopaque markers can be used to mark the location of blades 413 and 419. Other portions of catheter 401 can also be marked with radiopaque markers as necessary to allow for visualization of the location and position of parts of the catheter 401.

Figure 4B:
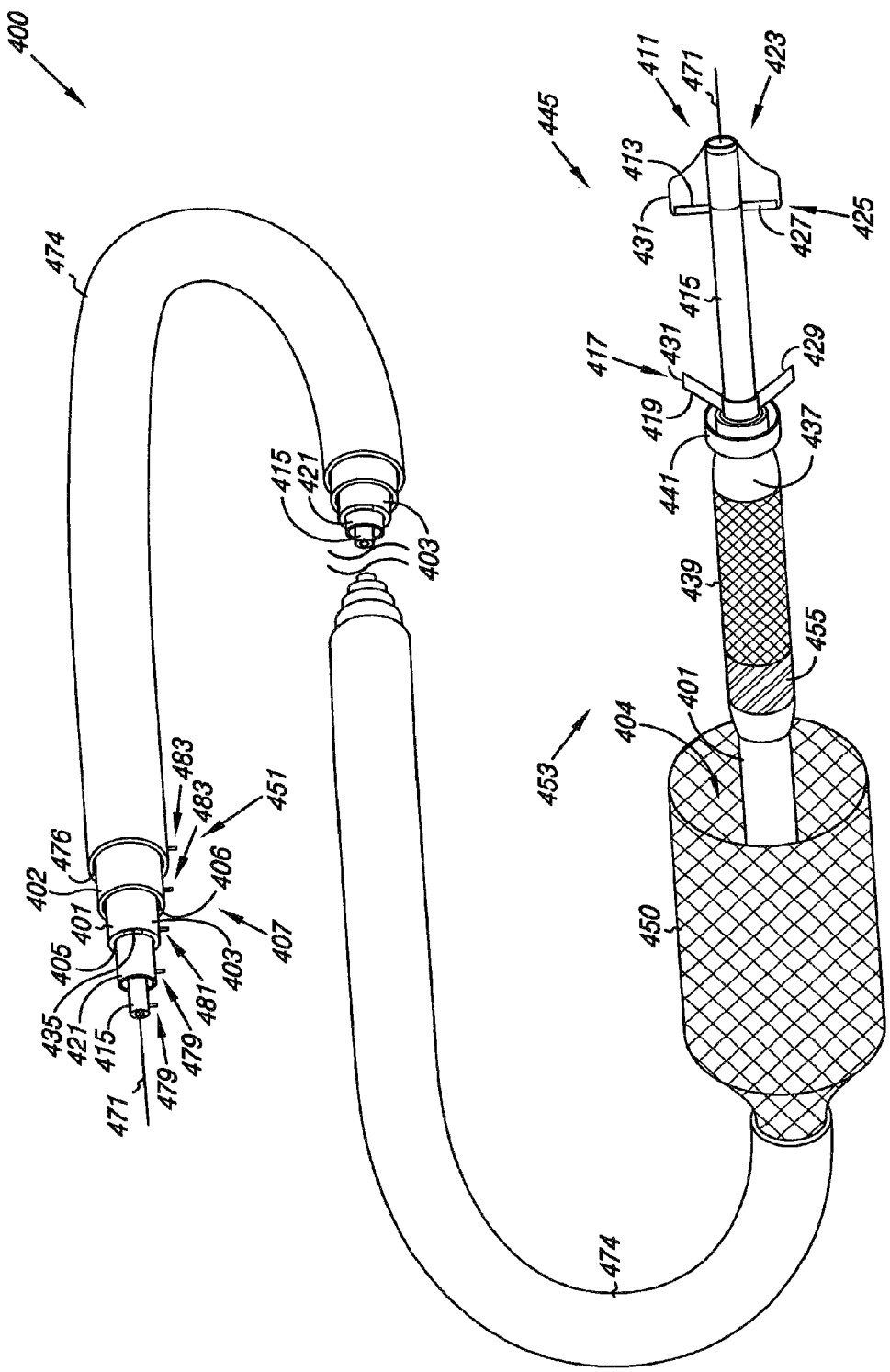

As illustrated in FIG. 4A, catheter 401 can reside at least partially within the lumen 406 of the elongate filter body. FIG. 4B provides an example in which both the valve 404 and the filter region 450 have been extended from the sheath 474, as discussed herein, with the catheter 401 at least partially extending distally from the valve 404. In the various embodiments, the valve leaflets of valve 404 can seat around the elongate body 403 of the catheter 401 to provide the reversibly sealable opening of the valve 404.

In the various embodiments, the elongate body 403 can travel longitudinally within the lumen 406 of the elongate filter body 402 to extend and retract the distal end 409 of the catheter 401 relative the valve 404 of the filter system 400. The elongate filter body 402 can further include a sealing ring that allows the elongate body 403 of the catheter 401 to move longitudinally while maintaining a fluid tight seal within the lumen 406 of the elongate filter body 402.

In addition to the structures described herein, the elongate body 403 of catheter 401 further includes a second lumen 435, as shown in FIG. 4A. In one embodiment, the second lumen 435 can extend between the proximal end 407 and the distal end 409 of the elongate body 403, where the second lumen 435 can be coupled in fluid tight communication to an inflatable balloon 437 on the elongate body 403. The catheter 401 can further include an inflation device 495 that can reversibly couple in fluid tight communication with the second lumen 435 to provide fluid pressure to inflate and deflate balloon 437.

Figure 4C:
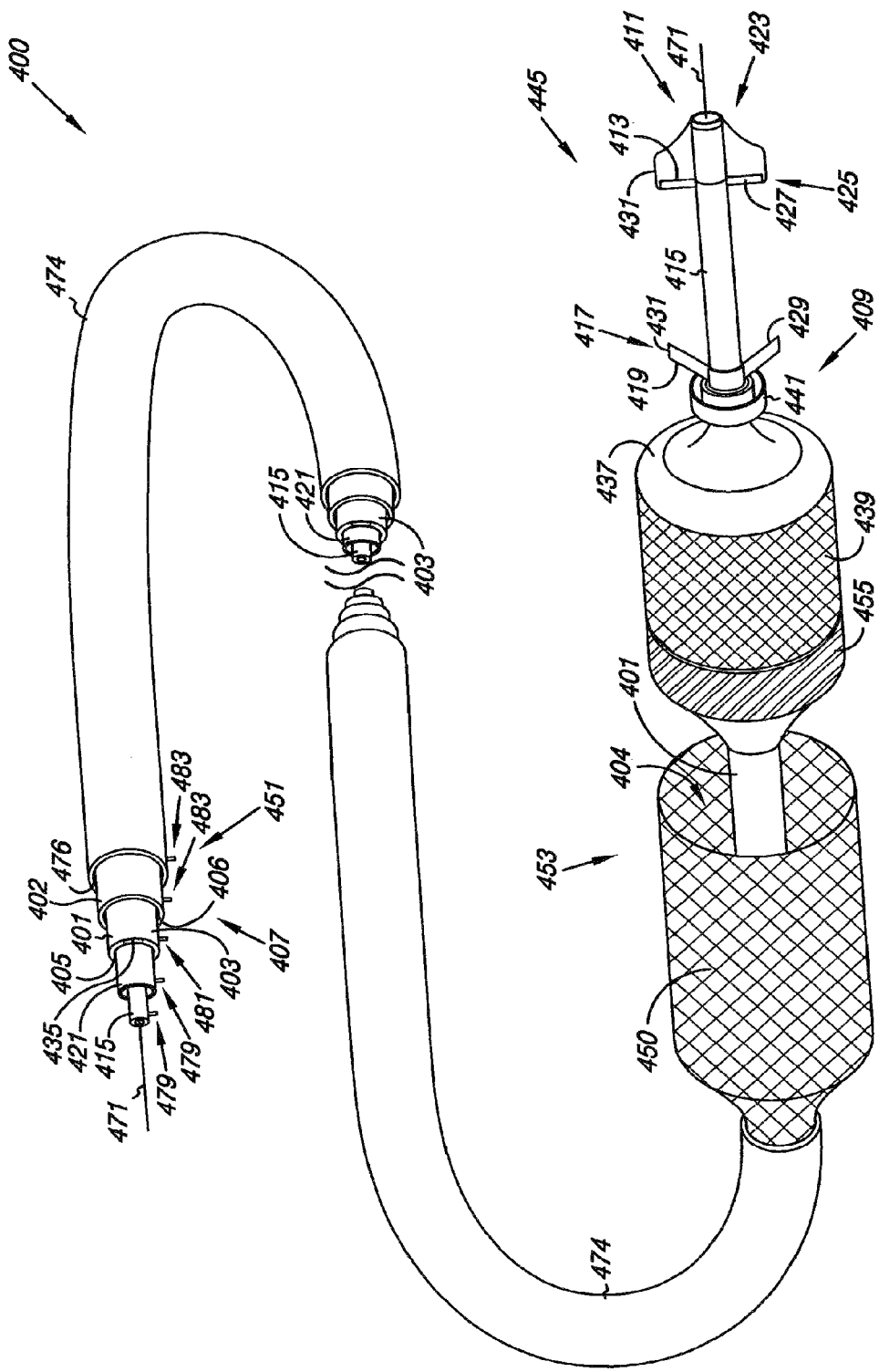

In one embodiment, the inflatable balloon 437 can be positioned adjacent the distal end 409 of the elongate body 403 and proximal to the second cutting head 417. The inflatable balloon 437 can be inflated from a deflated state to an inflated state by pressure applied by fluid moving through the second lumen 435. In addition, the catheter 401 further includes an expandable stent 439 positioned over at least a portion of the inflatable balloon 437. The expandable stent 439 can move between a compressed state, as shown in FIG. 4B, and an expanded state, as shown in FIG. 4C, using the inflatable balloon 437. In one embodiment, the expandable stent 439 can be deployed over cardiac tissue sheared using the first and second cutting heads 411 and 417 using the inflatable balloon 437.

Catheter 401 can further include an annular push ring 441 positioned between the second cutting head 417 and the inflatable balloon 437. The annular push ring 441 can be used for contacting and moving at least a portion of cardiac tissue sheared with the first and second cutting heads 411 and 417. For example, the first and second cutting heads 411 and 417 can be used to shear cardiac tissue (e.g., one or more cusps of a valve). The annular push ring 441 can then be advanced into contact with the sheared cardiac tissue. As the annular push ring 441 advances the sheared cardiac tissue can be directed towards the wall of the lumen. Stent 439 can then be positioned over at least a portion of the sheared cardiac tissue positioned using the annular push ring 441. Stent 439 can then be deployed using the inflatable balloon 437 to position at least a portion of the sheared cardiac tissue between the expanded stent 439 and the wall of the lumen. As will be appreciated, the dimensions and physical characteristics of the stent 439 will be dependent upon the location in which the stent 439 is to be implanted.

The apparatus 445 can further include a cardiac valve 455. The cardiac valve 455 can be releasably positioned adjacent the expandable stent 439 over at least a portion of the inflatable balloon 437. Generally, cardiac valve 455 can be implanted within the fluid passageway of a body lumen, such as for replacement of a valve structure within the body lumen to regulate the flow of a bodily fluid through the body lumen in a single direction.

Figure 4D:
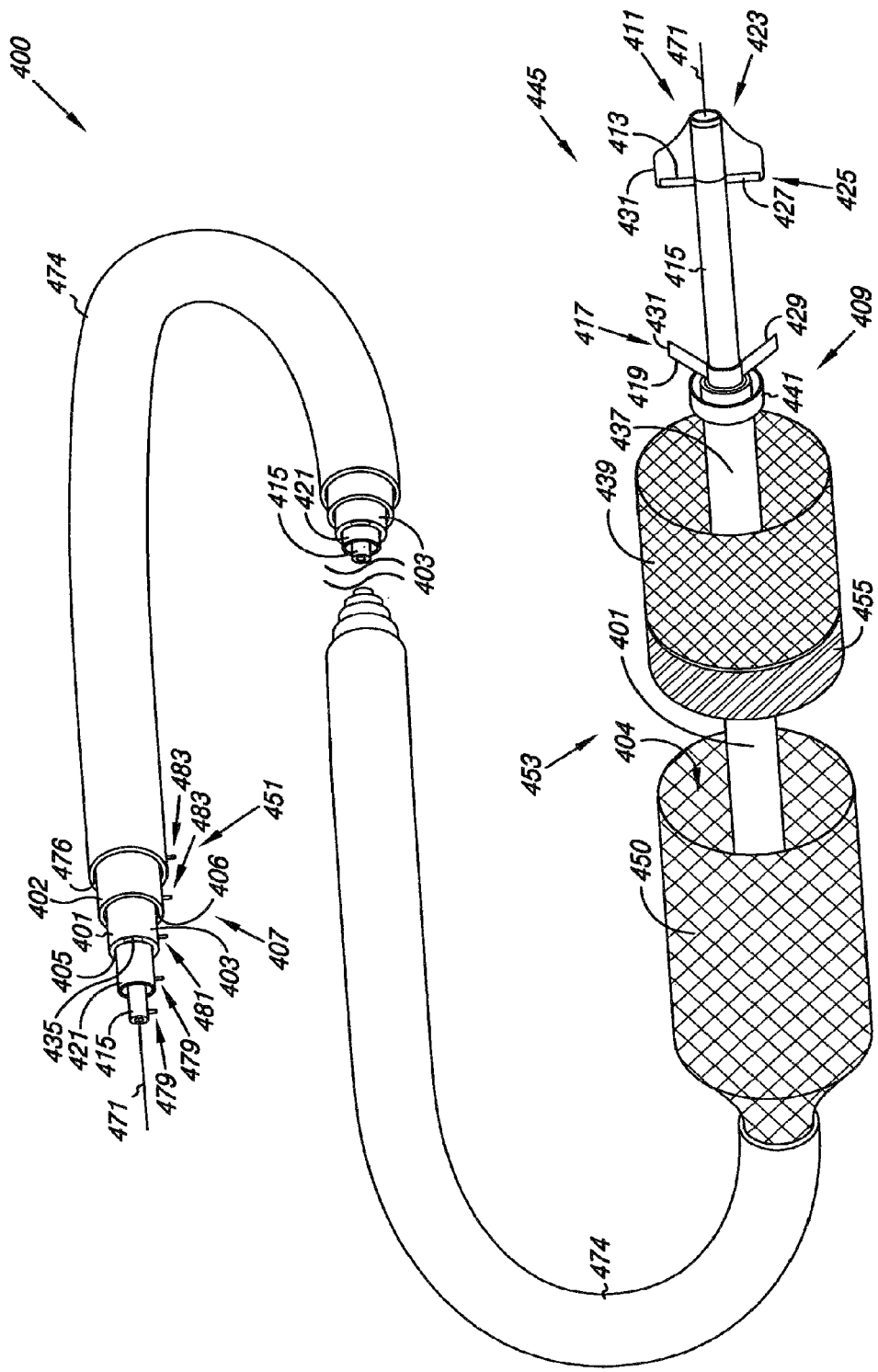

With respect to the apparatus 445, the cardiac valve 455 can be configured to reside in a compressed state over at least a portion of the inflatable balloon 437. Using the inflatable balloon, the cardiac valve 455 can be expanded into a deployed state as illustrated in FIGS. 4C and 4D.

One example of cardiac valve 455 includes valve 204 as described herein. An additional embodiment of cardiac valve 455 is illustrated in U.S. patent application Ser. No. 11/049,000, entitled "Vascular Catheter, System, and Method", which is hereby incorporated by reference in its entirety.

Generally, the cardiac valve 455 includes a support frame and a cover. The cover of the cardiac valve 455 can be positioned over at least the outer surface of the support frame. In one embodiment, the cover includes surfaces defining a reversibly sealable opening for unidirectional flow of a liquid through the lumen of the cardiac valve 455.

The filter system 400, catheter 401 and the apparatus 445 can further include handles to allow the various components to be moved relative each other. For example, handles 479 can allow the elongate pushing member 421 and/or the elongate pulling member 415 to be moved relative each other. Handle 481 can allow the catheter 401 to be moved relative the apparatus 445 and the sheath 474. In addition, handles 483 can allow the sheath 474 and the filter system 400 to be moved relative each other. As will be appreciated, other structures may be used in place of or in addition to the handles to allow the various components of the filter system 400, catheter 401, and apparatus 445 to move relative each other.

The embodiments of the present invention further include methods for forming the filter system and apparatus, as discussed herein. For example, embodiments of the present invention can be formed by providing an elongate filter body that includes the expandable filter region defining a lumen. The valve can further be provided, where the valve can be adjoined proximal the distal end of the elongate filter body to form a single lumen through which fluid flows unidirectionally through the valve and the elongate filter body to filter the fluid. As provided herein, the valve can define a reversibly sealable opening for the unidirectional flow of fluid through the lumen of the valve.

In one embodiment, the expandable filter region can be configured to move between a first configuration and a second configuration. In one embodiment, the movement from the first configuration to the second configuration can occur as the valve expands in addition to under pressure of the unidirectional flow of the fluid. The elongate filter body can also be provided with the fluid tight plug to direct the unidirectional flow of the fluid from the lumen through the expandable filter region to filter the unidirectional flow of the fluid. In these embodiments, the fluid tight plug can include various shapes and sizes and can be positioned according to the embodiments described herein.

In various embodiments, the valve can be provided with a support frame having various configurations. A first configuration can include a compressed configuration and a second configuration can include an expanded configuration. In various embodiments, expansion of the support frame can be supplemented by fluid flowing into the lumen of the elongate filter body.

The filter system and apparatus, as discussed herein, can further include providing the catheter having the first cutting head and the second cutting head, as discussed herein. The first cutting head can include the blade and the elongate pulling member, where the first cutting head can be positioned proximal the distal end of the elongate body with the elongate pulling member extending through the first lumen of the catheter. The elongate pulling member can then slides within the first lumen to move the first cutting head relative the distal end of the elongate body. The second cutting head can also include a blade, and be positioned adjacent the distal end of the elongate body between the distal end and the first cutting head. The blade of the first cutting head can be moved relative the blade of the second cutting head to provide the shearing action for cardiac tissue. The catheter extends though the lumen of the elongate filter body and the lumen of the valve.

In additional embodiments, the filter system and apparatus further include providing a second lumen to the elongate body, where the second lumen can be in fluid tight communication with the inflatable balloon positioned adjacent the distal end of the elongate body and proximal to the second cutting head. The expandable stent can then be positioned over at least a portion of the inflatable balloon, where the inflatable balloon deploys the expandable stent over sheared cardiac tissue. In further embodiment, the annular push ring can also be provided between the second cutting head and the inflatable balloon for contacting and moving at least a portion of the sheared cardiac tissue. The embodiments can also include providing the cardiac valve positioned over the inflatable balloon, where the cardiac valve can be deployed through the use of the inflatable balloon.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the support frame 120 and/or the cover 122 can be coated with a non-thrombogenic biocompatible material, as are known or will be known.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A filter system for use in a body lumen, comprising:
   an elongate filter body having a tubular shaft including an expandable filter region attached at a distal end of the shaft defining a lumen extending from a proximal end of the tubular shaft toward a distal end of the filter region, the expandable filter region; and
   a valve defining a valve lumen and having a reversibly sealable opening for unidirectional flow of a fluid through the valve lumen, the valve fixedly attached to the expandable filter region of the elongate filter body, the valve including a frame having a first elliptical member and a second elliptical member meeting at an angle;
   wherein the frame is radially movable between a compressed state and an expanded state;
   wherein the expandable filter region filters the unidirectional flow of the fluid passing through the valve lumen and the expandable filter region in the expanded state.

2. The filter system of claim 1, wherein the reversibly sealable opening is formed by one or more valve leaflets configured to move between an open configuration and a closed configuration.

3. The filter system of claim 2, wherein the valve includes a cover forming the one or more valve leaflets joined to the frame.

4. The filter system of claim 2, wherein the one or more valve leaflets are configured to open and close in response to fluid motion across the one or more valve leaflets.

5. The filter system of claim 2, wherein the one or more valve leaflets are configured to open and close in response to pressure differential across the one or more valve leaflets.

6. The filter system of claim 2, wherein the one or more valve leaflets include a first leaflet and a second leaflet coupled to the frame.

7. The filter system of claim 2, wherein the one or more valve leaflets are constructed from a fluid impermeable biocompatible material.

8. The filter system of claim 1, wherein the lumen of the filter body and the valve lumen are contiguous.

9. The filter system of claim 1, wherein the first elliptical member and the second elliptical member meet at a first region and a second region opposite the first region across a central axis of the valve lumen.

10. The filter system of claim 9, wherein the first region and the second region are positioned adjacent a minor axis of the first elliptical member and the second elliptical member.

11. The filter system of claim 9, wherein the first region and the second region are positioned away from a minor axis of the first elliptical member and the second elliptical member.

12. The filter system of claim 1, wherein the first elliptical member and the second elliptical member are configured to exert an expansion force against an inner wall of the body lumen in the expanded state.

13. The filter system of claim 1, wherein the expandable filter region is configured to trap particulate matter present in the unidirectional flow of the fluid passing through the valve lumen.

14. The filter system of claim 13, wherein the filter body is configured to remove particulate matter trapped by the expandable filter region through the tubular shaft.

15. The filter system of claim 1, wherein the valve is coupled to the expandable filter region proximal of a distal end of the elongate filter body.

16. The filter system of claim 15, wherein the expandable filter region is configured to radially self-expand from a compressed state to an expanded state when released from the compressed state.

17. The filter system of claim 1, wherein the expandable filter region include a woven configuration, a braided configuration, or a knit configuration.

18. The filter system of claim 1, wherein the elongate filter body further includes a fluid tight plug positioned within the lumen at the distal end of the tubular shaft.

19. The filter system of claim 18, wherein the fluid tight plug is positioned proximal of the expandable filter region, thereby directing the unidirectional flow of the fluid passing through the valve lumen through the expandable filter region.

* * * * *